(12) United States Patent
Bennett et al.

(10) Patent No.: US 12,201,520 B2
(45) Date of Patent: Jan. 21, 2025

(54) PROSTHETIC HEART VALVE

(71) Applicant: Edwards Lifesciences Corporation, Irvine, CA (US)

(72) Inventors: Nathan L. Bennett, Flagstaff, AZ (US); Joshua A. Sprinkle, Flagstaff, AZ (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 570 days.

(21) Appl. No.: 17/393,539

(22) Filed: Aug. 4, 2021

(65) Prior Publication Data

US 2021/0361420 A1 Nov. 25, 2021

Related U.S. Application Data

(63) Continuation of application No. 16/129,685, filed on Sep. 12, 2018, now Pat. No. 11,123,183.
(Continued)

(51) Int. Cl.
*A61F 2/24* (2006.01)

(52) U.S. Cl.
CPC .......... *A61F 2/2418* (2013.01); *A61F 2/2412* (2013.01); *A61F 2/2463* (2013.01); *A61F 2/2427* (2013.01); *A61F 2/246* (2013.01); *A61F 2/2466* (2013.01); *A61F 2210/0014* (2013.01); *A61F 2220/0016* (2013.01); *A61F 2220/005* (2013.01); *A61F 2220/0075* (2013.01); *A61F 2230/0069* (2013.01); *A61F 2250/0069* (2013.01)

(58) Field of Classification Search
CPC .... A61F 2/2418; A61F 2/2412; A61F 2/2463; A61F 2/2427; A61F 2/246; A61F 2/2466; A61F 2210/0014; A61F 2220/0016; A61F 2220/005; A61F 2220/0075; A61F 2230/0069; A61F 2250/0069; A61F 2/2409; A61F 2/2442; A61F 2/2445
See application file for complete search history.

(56) References Cited

U.S. PATENT DOCUMENTS

| 654,799 A | 7/1900 | Levett |
| 3,739,402 A | 6/1973 | Kahn et al. |
| (Continued) | | |

FOREIGN PATENT DOCUMENTS

| AU | 2013363172 A1 | 7/2015 |
| AU | 2017202405 A1 | 4/2017 |
| (Continued) | | |

OTHER PUBLICATIONS

Google Image Search Results, "S-Shaped", accessed Nov. 1, 2013.
(Continued)

*Primary Examiner* — Jerrah Edwards
*Assistant Examiner* — Jose H. Trevino, III
(74) *Attorney, Agent, or Firm* — Klarquist Sparkman, LLP; Sean Seung Kyu Kim

(57) ABSTRACT

Described embodiments are directed toward centrally-opening leaflet prosthetic valve devices having a leaflet frame and a leaflet construct including one or more leaflets. In some examples, the leaflet construct is coupled to the leaflet frame via a retention element. In some examples, the retention element is in the form of an outer frame that is coaxially arranged with the leaflet frame.

17 Claims, 13 Drawing Sheets

Related U.S. Application Data

(60) Provisional application No. 62/579,763, filed on Oct. 31, 2017.

(56) References Cited

U.S. PATENT DOCUMENTS

| | | | |
|---|---|---|---|
| 3,953,566 A | 4/1976 | Gore | |
| 4,178,639 A | 12/1979 | Bokros | |
| 4,187,390 A | 2/1980 | Gore | |
| 4,222,126 A | 9/1980 | Boretos et al. | |
| 4,265,694 A | 5/1981 | Boretos et al. | |
| 4,332,035 A | 6/1982 | Mano | |
| 4,340,091 A | 7/1982 | Skelton et al. | |
| 4,477,930 A | 10/1984 | Totten et al. | |
| 4,556,996 A | 12/1985 | Wallace | |
| 4,626,255 A | 12/1986 | Reichart et al. | |
| 4,759,759 A | 7/1988 | Walker et al. | |
| 4,851,000 A | 7/1989 | Gupta | |
| 4,877,661 A | 10/1989 | House et al. | |
| 4,955,899 A | 9/1990 | Della et al. | |
| 5,026,513 A | 6/1991 | House et al. | |
| 5,064,435 A | 11/1991 | Porter | |
| 5,071,609 A | 12/1991 | Tu et al. | |
| 5,123,918 A | 6/1992 | Perrier et al. | |
| 5,163,955 A | 11/1992 | Love et al. | |
| 5,415,667 A | 5/1995 | Frater | |
| 5,469,868 A | 11/1995 | Reger | |
| 5,476,589 A | 12/1995 | Bacino | |
| 5,489,297 A | 2/1996 | Duran | |
| 5,534,007 A | 7/1996 | St et al. | |
| 5,549,663 A | 8/1996 | Cottone, Jr. | |
| 5,554,183 A | 9/1996 | Nazari | |
| 5,554,185 A | 9/1996 | Block et al. | |
| 5,562,729 A | 10/1996 | Purdy | |
| 5,628,791 A | 5/1997 | Bokros et al. | |
| 5,673,102 A | 9/1997 | Suzuki et al. | |
| 5,708,044 A | 1/1998 | Branca | |
| 5,718,973 A | 2/1998 | Lewis et al. | |
| 5,749,852 A | 5/1998 | Schwab et al. | |
| 5,752,934 A | 5/1998 | Campbell et al. | |
| 5,759,192 A | 6/1998 | Saunders | |
| 5,769,884 A | 6/1998 | Solovay | |
| 5,772,884 A | 6/1998 | Tanaka et al. | |
| 5,788,626 A | 8/1998 | Thompson | |
| 5,814,405 A | 9/1998 | Branca et al. | |
| 5,824,043 A | 10/1998 | Cottone, Jr. | |
| 5,843,158 A | 12/1998 | Enker et al. | |
| 5,843,161 A | 12/1998 | Solovay | |
| 5,843,171 A | 12/1998 | Campbell et al. | |
| 5,853,419 A | 12/1998 | Imran | |
| 5,925,061 A | 7/1999 | Ogi et al. | |
| 5,928,281 A | 7/1999 | Huynh et al. | |
| 5,935,162 A | 8/1999 | Dang | |
| 5,935,163 A | 8/1999 | Gabbay | |
| 5,944,654 A | 8/1999 | Crawford | |
| 5,957,974 A | 9/1999 | Thompson et al. | |
| 6,010,529 A | 1/2000 | Herweck et al. | |
| 6,013,854 A | 1/2000 | Moriuchi | |
| 6,019,785 A | 2/2000 | Strecker | |
| 6,042,588 A | 3/2000 | Munsinger et al. | |
| 6,042,605 A | 3/2000 | Martin et al. | |
| 6,042,606 A | 3/2000 | Frantzen | |
| 6,086,612 A | 7/2000 | Jansen | |
| 6,110,198 A | 8/2000 | Fogarty et al. | |
| 6,117,169 A | 9/2000 | Moe | |
| 6,129,758 A | 10/2000 | Love | |
| 6,161,399 A | 12/2000 | Jayaraman | |
| 6,165,211 A | 12/2000 | Thompson | |
| 6,171,335 B1 | 1/2001 | Wheatley et al. | |
| 6,174,329 B1 | 1/2001 | Callol et al. | |
| 6,174,331 B1 | 1/2001 | Moe et al. | |
| 6,190,406 B1 | 2/2001 | Duerig et al. | |
| 6,197,143 B1 | 3/2001 | Bodnar | |
| 6,217,609 B1 | 4/2001 | Haverkost | |
| 6,245,012 B1 | 6/2001 | Kleshinski | |
| 6,261,320 B1 | 7/2001 | Tam et al. | |
| 6,261,620 B1 | 7/2001 | Leadbeater | |
| 6,283,994 B1 | 9/2001 | Moe et al. | |
| 6,283,995 B1 | 9/2001 | Moe et al. | |
| 6,287,334 B1 | 9/2001 | Moll et al. | |
| 6,328,763 B1 | 12/2001 | Love et al. | |
| 6,334,873 B1 | 1/2002 | Lane et al. | |
| 6,336,937 B1 | 1/2002 | Vonesh et al. | |
| 6,352,552 B1 | 3/2002 | Levinson et al. | |
| 6,379,382 B1 | 4/2002 | Yang | |
| 6,436,132 B1 | 8/2002 | Patel et al. | |
| 6,454,798 B1 | 9/2002 | Moe | |
| 6,454,799 B1 | 9/2002 | Schreck | |
| 6,461,382 B1 | 10/2002 | Cao | |
| 6,461,665 B1 | 10/2002 | Scholander | |
| 6,482,228 B1 | 11/2002 | Norred | |
| 6,488,701 B1 | 12/2002 | Nolting et al. | |
| 6,541,589 B1 | 4/2003 | Baillie | |
| 6,558,418 B2 | 5/2003 | Carpentier et al. | |
| 6,562,069 B2 | 5/2003 | Cai et al. | |
| 6,582,464 B2 | 6/2003 | Gabbay | |
| 6,613,086 B1 | 9/2003 | Moe et al. | |
| 6,620,190 B1 | 9/2003 | Colone | |
| 6,626,939 B1 | 9/2003 | Burnside et al. | |
| 6,645,244 B2 | 11/2003 | Shu et al. | |
| 6,666,885 B2 | 12/2003 | Moe | |
| 6,673,102 B1 | 1/2004 | Vonesh et al. | |
| 6,673,107 B1 | 1/2004 | Brandt et al. | |
| 6,726,715 B2 | 4/2004 | Sutherland | |
| 6,730,118 B2 | 5/2004 | Spenser et al. | |
| 6,730,120 B2 | 5/2004 | Berg et al. | |
| 6,755,856 B2 | 6/2004 | Fierens et al. | |
| 6,755,857 B2 | 6/2004 | Peterson et al. | |
| 6,758,858 B2 | 7/2004 | McCrea et al. | |
| 6,890,350 B1 | 5/2005 | Walak | |
| 6,893,460 B2 | 5/2005 | Spenser et al. | |
| 6,916,338 B2 | 7/2005 | Speziali | |
| 6,936,067 B2 | 8/2005 | Buchanan | |
| 6,953,332 B1 | 10/2005 | Kurk et al. | |
| 7,022,132 B2 | 4/2006 | Kocur | |
| 7,049,380 B1 | 5/2006 | Chang et al. | |
| 7,083,642 B2 | 8/2006 | Sirhan et al. | |
| 7,105,018 B1 | 9/2006 | Yip et al. | |
| 7,137,184 B2 | 11/2006 | Schreck | |
| 7,163,556 B2 | 1/2007 | Xie et al. | |
| 7,238,200 B2 | 7/2007 | Lee et al. | |
| 7,247,167 B2 | 7/2007 | Gabbay | |
| 7,306,729 B2 | 12/2007 | Bacino et al. | |
| 7,381,218 B2 | 6/2008 | Schreck | |
| 7,419,678 B2 | 9/2008 | Falotico | |
| 7,462,675 B2 | 12/2008 | Chang et al. | |
| 7,510,575 B2 | 3/2009 | Spenser et al. | |
| 7,513,909 B2 | 4/2009 | Lane et al. | |
| 7,531,611 B2 | 5/2009 | Sabol et al. | |
| 7,563,277 B2 | 7/2009 | Case et al. | |
| 7,708,775 B2 | 5/2010 | Rowe et al. | |
| 7,727,274 B2 | 6/2010 | Zilla et al. | |
| 7,758,640 B2 | 7/2010 | Vesely | |
| 7,780,725 B2 | 8/2010 | Haug et al. | |
| 7,789,908 B2 | 9/2010 | Sowinski et al. | |
| 7,803,186 B1 | 9/2010 | Li et al. | |
| 7,811,314 B2 | 10/2010 | Fierens et al. | |
| 7,815,763 B2 | 10/2010 | Fierens et al. | |
| 7,879,085 B2 | 2/2011 | Sowinski et al. | |
| 7,887,562 B2 | 2/2011 | Young et al. | |
| 7,914,569 B2 | 3/2011 | Nguyen et al. | |
| 7,927,364 B2 | 4/2011 | Fierens et al. | |
| 7,927,365 B2 | 4/2011 | Fierens et al. | |
| 7,935,141 B2 | 5/2011 | Randall et al. | |
| 7,967,829 B2 | 6/2011 | Gunderson et al. | |
| 7,967,853 B2 | 6/2011 | Eidenschink et al. | |
| 7,993,394 B2 | 8/2011 | Hariton et al. | |
| 8,048,440 B2 | 11/2011 | Chang et al. | |
| 8,062,359 B2 * | 11/2011 | Marquez | A61F 2/2409 623/2.38 |
| 8,092,523 B2 | 1/2012 | Li et al. | |
| 8,167,935 B2 | 5/2012 | Mcguckin et al. | |
| 8,226,710 B2 | 7/2012 | Nguyen et al. | |
| 8,246,678 B2 | 8/2012 | Salahieh et al. | |
| 8,252,037 B2 | 8/2012 | Styrc et al. | |

(56) References Cited

U.S. PATENT DOCUMENTS

| | | |
|---|---|---|
| 8,303,647 B2 | 11/2012 | Case |
| 8,349,000 B2 | 1/2013 | Schreck |
| 8,409,274 B2 | 4/2013 | Li et al. |
| 8,475,512 B2 | 7/2013 | Hunt |
| 8,545,525 B2 | 10/2013 | Surti et al. |
| 8,568,475 B2 | 10/2013 | Nguyen et al. |
| 8,585,753 B2 | 11/2013 | Scanlon et al. |
| 8,585,757 B2 | 11/2013 | Agathos |
| 8,628,566 B2 | 1/2014 | Eberhardt et al. |
| 8,637,144 B2 | 1/2014 | Ford |
| 8,709,077 B2 | 4/2014 | Schreck |
| 8,722,178 B2 | 5/2014 | Ashmead et al. |
| 8,728,103 B2 | 5/2014 | Surti et al. |
| 8,728,154 B2 | 5/2014 | Alkhatib |
| 8,784,481 B2 | 7/2014 | Alkhatib et al. |
| 8,801,774 B2 | 8/2014 | Silverman |
| 8,808,848 B2 | 8/2014 | Bacino |
| 8,845,709 B2 | 9/2014 | Styrc et al. |
| 8,845,721 B2 | 9/2014 | Braido et al. |
| 8,852,272 B2 | 10/2014 | Gross et al. |
| 8,870,948 B1 | 10/2014 | Erzberger et al. |
| 8,936,634 B2 | 1/2015 | Irwin et al. |
| 8,945,212 B2 | 2/2015 | Bruchman et al. |
| 8,961,599 B2 | 2/2015 | Bruchman et al. |
| 8,992,608 B2 | 3/2015 | Haug et al. |
| 9,039,757 B2 | 5/2015 | Mclean et al. |
| 9,101,469 B2 | 8/2015 | Bruchman et al. |
| 9,107,771 B2 | 8/2015 | Wubbeling et al. |
| 9,125,740 B2 | 9/2015 | Morriss et al. |
| 9,139,669 B2 | 9/2015 | Xu et al. |
| 9,144,492 B2 | 9/2015 | Bruchman et al. |
| 9,168,131 B2 | 10/2015 | Yohanan et al. |
| 9,198,787 B2 | 12/2015 | Kratzberg et al. |
| 9,241,695 B2 | 1/2016 | Peavey et al. |
| 9,283,072 B2 | 3/2016 | Bruchman et al. |
| 9,295,552 B2 | 3/2016 | Mclean et al. |
| 9,314,355 B2 | 4/2016 | Styrc et al. |
| 9,345,601 B2 | 5/2016 | Jantzen et al. |
| 9,375,308 B2 | 6/2016 | Norris |
| 9,393,110 B2 | 7/2016 | Levi et al. |
| 9,398,952 B2 | 7/2016 | Bruchman et al. |
| 9,399,085 B2 | 7/2016 | Cleek et al. |
| 9,504,565 B2 | 11/2016 | Armstrong |
| 9,554,786 B2 | 1/2017 | Carley et al. |
| 9,554,900 B2 | 1/2017 | Bruchman et al. |
| 9,597,181 B2 | 3/2017 | Christianson et al. |
| 9,629,718 B2 | 4/2017 | Gloss et al. |
| 9,681,948 B2 | 6/2017 | Levi et al. |
| 9,737,398 B2 | 8/2017 | Bruchman et al. |
| 9,737,422 B2 | 8/2017 | Armstrong et al. |
| 9,743,932 B2 | 8/2017 | Amplatz et al. |
| 9,795,496 B2 | 10/2017 | Armstrong et al. |
| 9,801,712 B2 | 10/2017 | Bruchman et al. |
| 9,827,089 B2 | 11/2017 | Bruchman et al. |
| 9,827,094 B2 | 11/2017 | Bennett |
| 9,839,540 B2 | 12/2017 | Armstrong et al. |
| 9,855,141 B2 | 1/2018 | Dienno et al. |
| 9,931,193 B2 | 4/2018 | Cully et al. |
| 9,931,204 B2 | 4/2018 | Rothstein et al. |
| 9,937,037 B2 | 4/2018 | Dienno et al. |
| 9,968,443 B2 | 5/2018 | Bruchman et al. |
| 10,039,638 B2 | 8/2018 | Bruchman et al. |
| 10,166,128 B2 | 1/2019 | Armstrong et al. |
| 10,279,084 B2 | 5/2019 | Goepfrich et al. |
| 10,285,808 B2 | 5/2019 | Bruchman et al. |
| 10,314,697 B2 | 6/2019 | Gassler |
| 10,321,986 B2 | 6/2019 | Bruchman et al. |
| 10,335,298 B2 | 7/2019 | Armstrong et al. |
| 10,342,659 B2 | 7/2019 | Bennett |
| 10,368,984 B2 | 8/2019 | Armstrong |
| 10,376,360 B2 | 8/2019 | Bruchman et al. |
| 10,441,416 B2 | 10/2019 | Oba et al. |
| 10,463,478 B2 | 11/2019 | Bruchman et al. |
| 10,507,124 B2 | 12/2019 | Armstrong et al. |
| 10,639,144 B2 | 5/2020 | Bruchman et al. |
| 10,660,745 B2 | 5/2020 | Bruchman et al. |
| 10,881,507 B2 | 1/2021 | Bruchman et al. |
| 10,980,633 B2 | 4/2021 | Dienno et al. |
| 11,020,221 B2 | 6/2021 | Arcaro et al. |
| 11,039,917 B2 | 6/2021 | Bruchman et al. |
| D926,322 S | 7/2021 | Bennett et al. |
| 11,065,112 B2 | 7/2021 | Gassler |
| 11,090,153 B2 | 8/2021 | Haarer et al. |
| 11,109,963 B2 | 9/2021 | Dienno et al. |
| 11,123,183 B2 | 9/2021 | Bennett et al. |
| 2001/0053929 A1 | 12/2001 | Vonesh et al. |
| 2002/0045936 A1 | 4/2002 | Moe |
| 2002/0055773 A1 | 5/2002 | Campbell et al. |
| 2002/0076542 A1 | 6/2002 | Kramer et al. |
| 2002/0082687 A1 | 6/2002 | Moe |
| 2002/0133226 A1 | 9/2002 | Marquez et al. |
| 2002/0183840 A1 | 12/2002 | Lapeyre et al. |
| 2002/0198588 A1 | 12/2002 | Armstrong et al. |
| 2002/0198594 A1 | 12/2002 | Schreck |
| 2003/0014105 A1 | 1/2003 | Cao |
| 2003/0027332 A1 | 2/2003 | Lafrance et al. |
| 2003/0055494 A1 | 3/2003 | Bezuidenhout et al. |
| 2003/0055496 A1 | 3/2003 | Cai et al. |
| 2003/0060871 A1 | 3/2003 | Hill et al. |
| 2003/0074052 A1 | 4/2003 | Besselink et al. |
| 2003/0097175 A1 | 5/2003 | O'Connor et al. |
| 2003/0114913 A1 | 6/2003 | Spenser et al. |
| 2003/0180488 A1 | 9/2003 | Lim et al. |
| 2003/0209835 A1 | 11/2003 | Chun et al. |
| 2003/0229394 A1 | 12/2003 | Ogle et al. |
| 2004/0024442 A1 | 2/2004 | Sowinski et al. |
| 2004/0024448 A1 | 2/2004 | Chang et al. |
| 2004/0024451 A1 | 2/2004 | Johnson et al. |
| 2004/0026245 A1 | 2/2004 | Agarwal et al. |
| 2004/0039436 A1 | 2/2004 | Spenser et al. |
| 2004/0044400 A1 | 3/2004 | Cheng et al. |
| 2004/0044401 A1 | 3/2004 | Bales et al. |
| 2004/0133266 A1 | 7/2004 | Clerc et al. |
| 2004/0170782 A1 | 9/2004 | Wang et al. |
| 2004/0176839 A1 | 9/2004 | Huynh et al. |
| 2004/0224442 A1 | 11/2004 | Grigg |
| 2004/0243222 A1 | 12/2004 | Osborne et al. |
| 2004/0260277 A1 | 12/2004 | Maguire |
| 2004/0260393 A1 | 12/2004 | Rahdert et al. |
| 2005/0027348 A1 | 2/2005 | Case et al. |
| 2005/0080476 A1 | 4/2005 | Gunderson et al. |
| 2005/0119722 A1 | 6/2005 | Styrc et al. |
| 2005/0137680 A1 | 6/2005 | Ortiz et al. |
| 2005/0137682 A1 | 6/2005 | Justino |
| 2005/0261765 A1 | 11/2005 | Liddicoat |
| 2005/0283224 A1 | 12/2005 | King |
| 2006/0008497 A1 | 1/2006 | Gabbay |
| 2006/0009835 A1 | 1/2006 | Osborne et al. |
| 2006/0015171 A1 | 1/2006 | Armstrong |
| 2006/0036311 A1 | 2/2006 | Nakayama et al. |
| 2006/0041091 A1 | 2/2006 | Chang et al. |
| 2006/0106337 A1 | 5/2006 | Blankenship |
| 2006/0118236 A1 | 6/2006 | House et al. |
| 2006/0122693 A1 | 6/2006 | Biadillah et al. |
| 2006/0135985 A1 | 6/2006 | Cox et al. |
| 2006/0154365 A1 | 7/2006 | Ratcliffe et al. |
| 2006/0161241 A1 | 7/2006 | Barbut et al. |
| 2006/0190070 A1 | 8/2006 | Dieck et al. |
| 2006/0229718 A1 | 10/2006 | Marquez |
| 2006/0229719 A1 | 10/2006 | Marquez et al. |
| 2006/0259133 A1 | 11/2006 | Sowinski et al. |
| 2006/0259136 A1 | 11/2006 | Nguyen et al. |
| 2006/0265053 A1 | 11/2006 | Hunt |
| 2006/0271091 A1 | 11/2006 | Campbell et al. |
| 2006/0276813 A1 | 12/2006 | Greenberg |
| 2006/0276883 A1 | 12/2006 | Greenberg et al. |
| 2006/0276888 A1 | 12/2006 | Lee et al. |
| 2006/0282162 A1 | 12/2006 | Nguyen et al. |
| 2006/0290027 A1 | 12/2006 | O'Connor et al. |
| 2007/0010876 A1 | 1/2007 | Salahieh et al. |
| 2007/0012624 A1 | 1/2007 | Bacino et al. |
| 2007/0021826 A1 | 1/2007 | Case et al. |
| 2007/0060999 A1 | 3/2007 | Randall et al. |
| 2007/0118210 A1 | 5/2007 | Pinchuk |

(56) References Cited

U.S. PATENT DOCUMENTS

| | | |
|---|---|---|
| 2007/0129786 A1 | 6/2007 | Beach et al. |
| 2007/0207186 A1 | 9/2007 | Scanlon et al. |
| 2007/0207816 A1 | 9/2007 | Spain, Jr. |
| 2007/0208421 A1 | 9/2007 | Quigley |
| 2007/0213800 A1 | 9/2007 | Fierens et al. |
| 2007/0244552 A1 | 10/2007 | Salahieh et al. |
| 2007/0250146 A1 | 10/2007 | Cully et al. |
| 2007/0250153 A1 | 10/2007 | Cully et al. |
| 2007/0254012 A1 | 11/2007 | Ludwig et al. |
| 2008/0009940 A1 | 1/2008 | Cribier |
| 2008/0026190 A1 | 1/2008 | King et al. |
| 2008/0039934 A1 | 2/2008 | Styrc |
| 2008/0051876 A1 | 2/2008 | Ta et al. |
| 2008/0065198 A1 | 3/2008 | Quintessenza |
| 2008/0071369 A1 | 3/2008 | Tuval et al. |
| 2008/0082154 A1 | 4/2008 | Tseng et al. |
| 2008/0097301 A1 | 4/2008 | Alpini et al. |
| 2008/0097401 A1 | 4/2008 | Trapp et al. |
| 2008/0097579 A1 | 4/2008 | Shanley et al. |
| 2008/0097582 A1 | 4/2008 | Shanley et al. |
| 2008/0119943 A1 | 5/2008 | Armstrong et al. |
| 2008/0133004 A1 | 6/2008 | White |
| 2008/0140178 A1 | 6/2008 | Rasmussen et al. |
| 2008/0195199 A1 | 8/2008 | Kheradvar et al. |
| 2008/0208327 A1 | 8/2008 | Rowe |
| 2008/0220041 A1 | 9/2008 | Brito et al. |
| 2008/0228263 A1 | 9/2008 | Ryan |
| 2008/0300678 A1 | 12/2008 | Eidenschink et al. |
| 2008/0319531 A1 | 12/2008 | Doran et al. |
| 2009/0005854 A1 | 1/2009 | Huang et al. |
| 2009/0030499 A1 | 1/2009 | Bebb et al. |
| 2009/0036976 A1 | 2/2009 | Beach et al. |
| 2009/0043373 A1 | 2/2009 | Arnault et al. |
| 2009/0104247 A1 | 4/2009 | Pacetti |
| 2009/0117334 A1 | 5/2009 | Sogard et al. |
| 2009/0138079 A1 | 5/2009 | Tuval et al. |
| 2009/0157175 A1 | 6/2009 | Benichou |
| 2009/0182413 A1 | 7/2009 | Burkart et al. |
| 2009/0240320 A1 | 9/2009 | Tuval et al. |
| 2009/0264997 A1 | 10/2009 | Salahieh et al. |
| 2009/0276039 A1 | 11/2009 | Meretei |
| 2009/0287305 A1 | 11/2009 | Amalaha |
| 2009/0292350 A1 | 11/2009 | Eberhardt et al. |
| 2009/0306762 A1 | 12/2009 | Mccullagh et al. |
| 2009/0306766 A1 | 12/2009 | Mcdermott et al. |
| 2010/0016940 A1 | 1/2010 | Shokoohi et al. |
| 2010/0023114 A1 | 1/2010 | Chambers et al. |
| 2010/0036021 A1 | 2/2010 | Lee et al. |
| 2010/0036484 A1 | 2/2010 | Hariton et al. |
| 2010/0049294 A1 | 2/2010 | Zukowski et al. |
| 2010/0082094 A1 | 4/2010 | Quadri et al. |
| 2010/0094394 A1 | 4/2010 | Beach et al. |
| 2010/0094405 A1 | 4/2010 | Cottone |
| 2010/0106240 A1 | 4/2010 | Duggal et al. |
| 2010/0131056 A1 | 5/2010 | Lapeyre |
| 2010/0137998 A1 | 6/2010 | Sobrino-Serrano et al. |
| 2010/0145438 A1 | 6/2010 | Barone |
| 2010/0159171 A1 | 6/2010 | Clough |
| 2010/0168839 A1 | 7/2010 | Braido et al. |
| 2010/0185274 A1 | 7/2010 | Moaddeb et al. |
| 2010/0185277 A1 | 7/2010 | Braido et al. |
| 2010/0191320 A1 | 7/2010 | Straubinger et al. |
| 2010/0204781 A1 | 8/2010 | Alkhatib |
| 2010/0204785 A1 | 8/2010 | Alkhatib |
| 2010/0211165 A1 | 8/2010 | Schreck |
| 2010/0217382 A1 | 8/2010 | Chau et al. |
| 2010/0248324 A1 | 9/2010 | Xu et al. |
| 2010/0249923 A1 | 9/2010 | Alkhatib et al. |
| 2010/0256738 A1 | 10/2010 | Berglund |
| 2010/0262231 A1 | 10/2010 | Tuval et al. |
| 2010/0286760 A1 | 11/2010 | Beach et al. |
| 2010/0298931 A1 | 11/2010 | Quadri et al. |
| 2010/0305682 A1 | 12/2010 | Furst |
| 2011/0009953 A1 | 1/2011 | Luk et al. |
| 2011/0040366 A1 | 2/2011 | Goetz et al. |
| 2011/0054515 A1 | 3/2011 | Bridgeman et al. |
| 2011/0064781 A1 | 3/2011 | Cleek et al. |
| 2011/0087318 A1 | 4/2011 | Daugherty et al. |
| 2011/0160836 A1 | 6/2011 | Behan |
| 2011/0172784 A1 | 7/2011 | Richter et al. |
| 2011/0208283 A1 | 8/2011 | Rust |
| 2011/0218619 A1 | 9/2011 | Benichou et al. |
| 2011/0251678 A1 | 10/2011 | Eidenschink et al. |
| 2011/0257739 A1 | 10/2011 | Corbett |
| 2011/0282439 A1 | 11/2011 | Thill et al. |
| 2011/0295363 A1 | 12/2011 | Girard et al. |
| 2012/0035722 A1 | 2/2012 | Tuval |
| 2012/0078357 A1 | 3/2012 | Conklin |
| 2012/0083839 A1 | 4/2012 | Letac et al. |
| 2012/0089223 A1 | 4/2012 | Nguyen et al. |
| 2012/0101567 A1 | 4/2012 | Jansen |
| 2012/0101571 A1 | 4/2012 | Thambar et al. |
| 2012/0116496 A1 | 5/2012 | Chuter et al. |
| 2012/0116498 A1 | 5/2012 | Chuter et al. |
| 2012/0123529 A1 | 5/2012 | Levi et al. |
| 2012/0123530 A1 | 5/2012 | Carpentier et al. |
| 2012/0130468 A1 | 5/2012 | Khosravi et al. |
| 2012/0130471 A1 | 5/2012 | Shoemaker et al. |
| 2012/0185038 A1 | 7/2012 | Fish et al. |
| 2012/0215303 A1 | 8/2012 | Quadri et al. |
| 2012/0253453 A1 | 10/2012 | Bruchman et al. |
| 2012/0290082 A1 | 11/2012 | Quint et al. |
| 2012/0323211 A1 | 12/2012 | Ogle et al. |
| 2012/0323315 A1 | 12/2012 | Bruchman et al. |
| 2013/0018456 A1 | 1/2013 | Li et al. |
| 2013/0018458 A1 | 1/2013 | Yohanan et al. |
| 2013/0079700 A1 | 3/2013 | Ballard et al. |
| 2013/0110229 A1 | 5/2013 | Bokeriya et al. |
| 2013/0116655 A1 | 5/2013 | Bacino et al. |
| 2013/0131780 A1 | 5/2013 | Armstrong et al. |
| 2013/0150956 A1 | 6/2013 | Yohanan et al. |
| 2013/0158647 A1 | 6/2013 | Norris et al. |
| 2013/0166021 A1 | 6/2013 | Bruchman et al. |
| 2013/0183515 A1 | 7/2013 | White |
| 2013/0184807 A1 | 7/2013 | Kovach et al. |
| 2013/0197624 A1 | 8/2013 | Armstrong et al. |
| 2013/0204347 A1 | 8/2013 | Armstrong et al. |
| 2013/0204360 A1 | 8/2013 | Gainor |
| 2013/0253466 A1 | 9/2013 | Campbell et al. |
| 2013/0297003 A1 | 11/2013 | Pinchuk |
| 2013/0338755 A1 | 12/2013 | Goetz et al. |
| 2014/0005771 A1 | 1/2014 | Braido et al. |
| 2014/0005773 A1 | 1/2014 | Wheatley |
| 2014/0031924 A1 | 1/2014 | Bruchman et al. |
| 2014/0031927 A1 | 1/2014 | Bruchman et al. |
| 2014/0094898 A1 | 4/2014 | Borck |
| 2014/0106951 A1 | 4/2014 | Brandon |
| 2014/0135897 A1 | 5/2014 | Cully et al. |
| 2014/0163671 A1 | 6/2014 | Bruchman et al. |
| 2014/0163673 A1 | 6/2014 | Bruchman et al. |
| 2014/0172066 A1 | 6/2014 | Goepfrich et al. |
| 2014/0172069 A1 | 6/2014 | Roeder et al. |
| 2014/0172077 A1 | 6/2014 | Bruchman et al. |
| 2014/0172078 A1 | 6/2014 | Bruchman et al. |
| 2014/0172079 A1 | 6/2014 | Bruchman et al. |
| 2014/0172082 A1 | 6/2014 | Bruchman et al. |
| 2014/0172083 A1 | 6/2014 | Bruchman et al. |
| 2014/0180400 A1 | 6/2014 | Bruchman et al. |
| 2014/0180402 A1 | 6/2014 | Bruchman et al. |
| 2014/0194968 A1 | 7/2014 | Zukowski |
| 2014/0222140 A1 | 8/2014 | Schreck |
| 2014/0236289 A1 | 8/2014 | Alkhatib |
| 2014/0277413 A1 | 9/2014 | Arnold et al. |
| 2014/0277418 A1 | 9/2014 | Miller |
| 2014/0296969 A1 | 10/2014 | Tegels et al. |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0343670 A1 | 11/2014 | Bakis et al. |
| 2015/0005870 A1 | 1/2015 | Kovach et al. |
| 2015/0018944 A1 | 1/2015 | O'Connell et al. |
| 2015/0088250 A1 | 3/2015 | Zeng et al. |
| 2015/0105856 A1 | 4/2015 | Rowe et al. |
| 2015/0142100 A1 | 5/2015 | Morriss et al. |

(56) References Cited

U.S. PATENT DOCUMENTS

| | | |
|---|---|---|
| 2015/0157456 A1 | 6/2015 | Armstrong |
| 2015/0157770 A1 | 6/2015 | Cully et al. |
| 2015/0224231 A1 | 8/2015 | Bruchman et al. |
| 2015/0245910 A1 | 9/2015 | Righini et al. |
| 2015/0313871 A1 | 11/2015 | Li et al. |
| 2015/0366663 A1 | 12/2015 | Bruchman et al. |
| 2015/0366664 A1 | 12/2015 | Guttenberg et al. |
| 2016/0001469 A1 | 1/2016 | Bacchereti et al. |
| 2016/0015422 A1 | 1/2016 | De et al. |
| 2016/0074161 A1* | 3/2016 | Bennett .............. A61F 2/2412 29/890.126 |
| 2016/0113699 A1 | 4/2016 | Sverdlik et al. |
| 2016/0157998 A1 | 6/2016 | Bruchman et al. |
| 2016/0175095 A1 | 6/2016 | Dienno et al. |
| 2016/0175096 A1 | 6/2016 | Dienno et al. |
| 2016/0206424 A1 | 7/2016 | Al-Jilaihawi et al. |
| 2016/0213465 A1 | 7/2016 | Girard et al. |
| 2016/0235525 A1 | 8/2016 | Rothstein et al. |
| 2016/0310268 A1 | 10/2016 | Oba et al. |
| 2016/0317299 A1 | 11/2016 | Alkhatib |
| 2017/0027727 A1 | 2/2017 | Wuebbeling et al. |
| 2017/0042674 A1 | 2/2017 | Armstrong |
| 2017/0056169 A1 | 3/2017 | Johnson et al. |
| 2017/0065400 A1 | 3/2017 | Armstrong et al. |
| 2017/0095330 A1 | 4/2017 | Malewicz et al. |
| 2017/0095331 A1 | 4/2017 | Spenser et al. |
| 2017/0100236 A1 | 4/2017 | Robertson et al. |
| 2017/0105854 A1 | 4/2017 | Treacy et al. |
| 2017/0106176 A1 | 4/2017 | Taft et al. |
| 2017/0128199 A1 | 5/2017 | Gurovich et al. |
| 2017/0156859 A1 | 6/2017 | Chang et al. |
| 2017/0165066 A1 | 6/2017 | Rothstein |
| 2017/0165067 A1 | 6/2017 | Barajas-Torres et al. |
| 2017/0216062 A1 | 8/2017 | Armstrong et al. |
| 2017/0224481 A1 | 8/2017 | Spenser et al. |
| 2017/0252153 A1 | 9/2017 | Chau et al. |
| 2017/0348101 A1 | 12/2017 | Vaughn et al. |
| 2018/0021128 A1 | 1/2018 | Bruchman et al. |
| 2018/0021129 A1 | 1/2018 | Peterson et al. |
| 2018/0125646 A1 | 5/2018 | Bruchman et al. |
| 2018/0177583 A1 | 6/2018 | Cully et al. |
| 2018/0221144 A1 | 8/2018 | Bruchman et al. |
| 2018/0318070 A1 | 11/2018 | Bruchman et al. |
| 2019/0076245 A1 | 3/2019 | Arcaro et al. |
| 2019/0091014 A1 | 3/2019 | Arcaro et al. |
| 2019/0091015 A1 | 3/2019 | Dienno et al. |
| 2019/0110893 A1 | 4/2019 | Haarer et al. |
| 2019/0125517 A1 | 5/2019 | Cully et al. |
| 2019/0125528 A1 | 5/2019 | Busalacchi et al. |
| 2019/0125530 A1 | 5/2019 | Arcaro et al. |
| 2019/0125531 A1 | 5/2019 | Bennett et al. |
| 2019/0125534 A1 | 5/2019 | Arcaro et al. |
| 2019/0209292 A1 | 7/2019 | Bruchman et al. |
| 2019/0209739 A1 | 7/2019 | Goepfrich et al. |
| 2019/0216592 A1 | 7/2019 | Cully et al. |
| 2019/0247185 A1 | 8/2019 | Gassler |
| 2019/0254815 A1 | 8/2019 | Bruchman et al. |
| 2019/0269505 A1 | 9/2019 | Bruchman et al. |
| 2019/0314154 A1 | 10/2019 | Armstrong |
| 2019/0328525 A1 | 10/2019 | Noe et al. |
| 2019/0374339 A1 | 12/2019 | Bennett |
| 2020/0000578 A1 | 1/2020 | Bruchman et al. |
| 2020/0022828 A1 | 1/2020 | Armstrong et al. |
| 2020/0179663 A1 | 6/2020 | Mcdaniel et al. |
| 2020/0237497 A1 | 7/2020 | Silverman et al. |
| 2020/0237505 A1 | 7/2020 | Bruchman et al. |
| 2020/0246137 A1 | 8/2020 | Bruchman et al. |
| 2020/0276014 A1 | 9/2020 | Burkart et al. |
| 2021/0121289 A1 | 4/2021 | Bruchman et al. |
| 2021/0177589 A1 | 6/2021 | Arcaro et al. |
| 2021/0205074 A1 | 7/2021 | Bruchman et al. |
| 2021/0307905 A1 | 10/2021 | Arcaro et al. |
| 2021/0338422 A1 | 11/2021 | Dienno et al. |
| 2021/0346156 A1 | 11/2021 | Haarer et al. |
| 2021/0393399 A1 | 12/2021 | Arcaro et al. |
| 2022/0000611 A1 | 1/2022 | Arcaro et al. |
| 2022/0023032 A1 | 1/2022 | Bruchman et al. |

FOREIGN PATENT DOCUMENTS

| | | |
|---|---|---|
| CA | 2462509 A1 | 4/2003 |
| CA | 2849030 A1 | 4/2013 |
| CA | 2878691 A1 | 1/2014 |
| CA | 2964546 A1 | 1/2014 |
| CA | 2960034 A1 | 3/2016 |
| CN | 101057796 A | 10/2007 |
| CN | 101091675 A | 12/2007 |
| CN | 101188985 A | 5/2008 |
| CN | 101420913 A | 4/2009 |
| CN | 101849863 A | 10/2010 |
| CN | 101902989 A | 12/2010 |
| CN | 101926699 A | 12/2010 |
| CN | 201744060 U | 2/2011 |
| CN | 102015009 A | 4/2011 |
| CN | 102119013 A | 7/2011 |
| CN | 102292053 A | 12/2011 |
| CN | 102438546 A | 5/2012 |
| CN | 102573703 A | 7/2012 |
| CN | 102652694 A | 9/2012 |
| CN | 102764169 A | 11/2012 |
| CN | 102791223 A | 11/2012 |
| CN | 102883684 A | 1/2013 |
| CN | 103079498 A | 5/2013 |
| CN | 103228232 A | 7/2013 |
| CN | 103237524 A | 8/2013 |
| CN | 103384505 A | 11/2013 |
| CN | 103732183 A | 4/2014 |
| CN | 103781439 A | 5/2014 |
| CN | 103945796 A | 7/2014 |
| CN | 104114127 A | 10/2014 |
| CN | 104487023 A | 4/2015 |
| CN | 104507417 A | 4/2015 |
| CN | 104869948 A | 8/2015 |
| CN | 105007955 A | 10/2015 |
| CN | 105101911 A | 11/2015 |
| CN | 105263445 A | 1/2016 |
| CN | 105662651 A | 6/2016 |
| CN | 105792780 A | 7/2016 |
| CN | 106714733 A | 5/2017 |
| CN | 106794065 A | 5/2017 |
| CN | 107106294 A | 8/2017 |
| CN | 107690323 A | 2/2018 |
| DE | 212013000104 U1 | 11/2014 |
| EP | 0293090 A2 | 11/1988 |
| EP | 0313263 A2 | 4/1989 |
| EP | 0582870 A2 | 2/1994 |
| EP | 0775472 A2 | 5/1997 |
| EP | 0815806 A2 | 1/1998 |
| EP | 0893108 A2 | 1/1999 |
| EP | 1318775 A1 | 6/2003 |
| EP | 1666003 A1 | 6/2006 |
| EP | 1395205 B1 | 7/2008 |
| EP | 1235537 B1 | 12/2008 |
| EP | 2193762 A1 | 6/2010 |
| EP | 2255750 A2 | 12/2010 |
| EP | 2400923 A1 | 1/2012 |
| EP | 2359774 B1 | 1/2013 |
| EP | 2591100 A2 | 5/2013 |
| EP | 2109417 B1 | 11/2013 |
| EP | 3142608 A1 | 3/2017 |
| EP | 3797738 A1 | 3/2021 |
| FR | 2591100 A1 | 6/1987 |
| GB | 2312485 A | 10/1997 |
| GB | 2513194 A | 10/2014 |
| IN | 101374477 A | 2/2009 |
| IN | 106668949 A | 5/2017 |
| JP | 44-032400 | 12/1969 |
| JP | 1969-032400 B | 12/1969 |
| JP | 02-000645 A | 1/1990 |
| JP | 09-241412 A | 9/1997 |
| JP | 10-507097 A | 7/1998 |
| JP | 11-290448 A | 10/1999 |
| JP | 11-512635 A | 11/1999 |

(56) References Cited

FOREIGN PATENT DOCUMENTS

| | | |
|---|---|---|
| JP | 2000-511459 A | 9/2000 |
| JP | 2000-513248 A | 10/2000 |
| JP | 2001-508641 A | 7/2001 |
| JP | 2001-508681 A | 7/2001 |
| JP | 2001-509702 A | 7/2001 |
| JP | 2001-511030 A | 8/2001 |
| JP | 2002-525169 A | 8/2002 |
| JP | 2002-541915 A | 12/2002 |
| JP | 2004-510471 A | 4/2004 |
| JP | 2005-500101 A | 1/2005 |
| JP | 2005-512611 A | 5/2005 |
| JP | 2007-526098 A | 9/2007 |
| JP | 2007-536989 A | 12/2007 |
| JP | 2008-506459 A | 3/2008 |
| JP | 2008-535572 A | 9/2008 |
| JP | 4335487 B2 | 9/2009 |
| JP | 2010-500107 A | 1/2010 |
| JP | 2010-504174 A | 2/2010 |
| JP | 2010-517623 A | 5/2010 |
| JP | 2010-528761 A | 8/2010 |
| JP | 2010-188189 A | 9/2010 |
| JP | 2010-535075 A | 11/2010 |
| JP | 2010-536527 A | 12/2010 |
| JP | 2012-504031 A | 2/2012 |
| JP | 2012-152563 A | 8/2012 |
| JP | 2013-543399 A | 12/2013 |
| JP | 2014-513585 A | 6/2014 |
| JP | 2014-517720 A | 7/2014 |
| JP | 2016-501104 A | 1/2016 |
| JP | 2016-518948 A | 6/2016 |
| JP | 2017-527397 A | 9/2017 |
| JP | 2018-079352 A | 5/2018 |
| JP | 6392778 B2 | 9/2018 |
| JP | 6802300 B2 | 12/2020 |
| NO | 2014/099150 A1 | 6/2014 |
| RU | 2124986 C1 | 1/1999 |
| RU | 2434604 C1 | 11/2011 |
| WO | 94/13224 A1 | 6/1994 |
| WO | 94/16802 A1 | 8/1994 |
| WO | 95/05555 A1 | 2/1995 |
| WO | 95/09586 A1 | 4/1995 |
| WO | 96/02212 A1 | 2/1996 |
| WO | 96/07370 A1 | 3/1996 |
| WO | 96/40348 A1 | 12/1996 |
| WO | 97/10871 A1 | 3/1997 |
| WO | 99/26558 A1 | 6/1999 |
| WO | 00/18333 A1 | 4/2000 |
| WO | 00/41649 A1 | 7/2000 |
| WO | 00/47271 A1 | 8/2000 |
| WO | 00/62716 A1 | 10/2000 |
| WO | 01/28453 A2 | 4/2001 |
| WO | 01/41679 A1 | 6/2001 |
| WO | 01/64278 A1 | 9/2001 |
| WO | 01/74272 A2 | 10/2001 |
| WO | 02/07795 A2 | 1/2002 |
| WO | 02/24118 A1 | 3/2002 |
| WO | 02/24119 A1 | 3/2002 |
| WO | 02/45933 A2 | 6/2002 |
| WO | 02/47468 A1 | 6/2002 |
| WO | 02/60506 A1 | 8/2002 |
| WO | 2002/100301 A1 | 12/2002 |
| WO | 03/03946 A1 | 1/2003 |
| WO | 03/07795 A2 | 1/2003 |
| WO | 03/47468 A1 | 6/2003 |
| WO | 03/90834 A2 | 11/2003 |
| WO | 2004/000375 A1 | 12/2003 |
| WO | 2005/112827 A2 | 12/2005 |
| WO | 2006/019626 A2 | 2/2006 |
| WO | 2006/058322 A2 | 6/2006 |
| WO | 2006/108090 A2 | 10/2006 |
| WO | 2007/016251 A2 | 2/2007 |
| WO | 2008/021002 A1 | 2/2008 |
| WO | 2008/028964 A2 | 3/2008 |
| WO | 2008/036870 A2 | 3/2008 |
| WO | 2008/049045 A2 | 4/2008 |
| WO | 2008/052421 A1 | 5/2008 |
| WO | 2008/091589 A1 | 7/2008 |
| WO | 2008/021006 A3 | 8/2008 |
| WO | 2008/097589 A1 | 8/2008 |
| WO | 2008/097592 A2 | 8/2008 |
| WO | 2008/150529 A1 | 12/2008 |
| WO | 2009/017827 A1 | 2/2009 |
| WO | 2009/029199 A1 | 3/2009 |
| WO | 2009/045332 A2 | 4/2009 |
| WO | 2009/100210 A1 | 8/2009 |
| WO | 2009/108355 A1 | 9/2009 |
| WO | 2010/006783 A1 | 1/2010 |
| WO | 2010/008570 A1 | 1/2010 |
| WO | 2010/030766 A1 | 3/2010 |
| WO | 2010/037141 A1 | 4/2010 |
| WO | 2010/057262 A1 | 5/2010 |
| WO | 2010/086460 A1 | 8/2010 |
| WO | 2010/132707 A1 | 11/2010 |
| WO | 2010/150208 A2 | 12/2010 |
| WO | 2011/098565 A1 | 8/2011 |
| WO | 2011/109450 A2 | 9/2011 |
| WO | 2011/109801 A2 | 9/2011 |
| WO | 2011/112706 A2 | 9/2011 |
| WO | 2012/004460 A2 | 1/2012 |
| WO | 2012/011261 A1 | 1/2012 |
| WO | 2012/040643 A2 | 3/2012 |
| WO | 2012/047644 A2 | 4/2012 |
| WO | 2012/065080 A2 | 5/2012 |
| WO | 2012/082952 A2 | 6/2012 |
| WO | 2012/099979 A1 | 7/2012 |
| WO | 2012/110767 A2 | 8/2012 |
| WO | 2012/116368 A2 | 8/2012 |
| WO | 2012/135603 A2 | 10/2012 |
| WO | 2012/158944 A1 | 11/2012 |
| WO | 2012/167131 A1 | 12/2012 |
| WO | 2013/074663 A2 | 5/2013 |
| WO | 2013/074990 A1 | 5/2013 |
| WO | 2013/096854 A2 | 6/2013 |
| WO | 2013/109337 A1 | 7/2013 |
| WO | 2014/018189 A2 | 1/2014 |
| WO | 2014/018432 A2 | 1/2014 |
| WO | 2014/099163 A1 | 6/2014 |
| WO | 2014/099722 A1 | 6/2014 |
| WO | 2014/144937 A2 | 9/2014 |
| WO | 2015/045002 A1 | 4/2015 |
| WO | 2015/085138 A1 | 6/2015 |
| WO | 2015/171743 A2 | 11/2015 |
| WO | 2015/173794 A1 | 11/2015 |
| WO | 2016/028591 A1 | 2/2016 |
| WO | 2016/044223 A1 | 3/2016 |
| WO | 2016/100913 A1 | 6/2016 |
| WO | 2016/172349 A1 | 10/2016 |
| WO | 2016/186909 A1 | 11/2016 |
| WO | 2017/038145 A1 | 3/2017 |
| WO | 2017/096157 A1 | 6/2017 |
| WO | 2019/067219 A1 | 4/2019 |
| WO | 2019/067220 A1 | 4/2019 |
| WO | 2019/074607 A1 | 4/2019 |
| WO | 2019/074869 A1 | 4/2019 |
| WO | 2019/089138 A1 | 5/2019 |

OTHER PUBLICATIONS

International Preliminary Report on Patentability received for PCT Patent Application No. PCT/US15/50113, mailed on Mar. 30, 2017, 9 pages.

International Preliminary Report on Patentability received for PCT Patent Application No. PCT/US2020/027921, mailed on Oct. 21, 2021, 11 pages.

International Search Report and Written Opinion received for PCT Patent Application No. PCT/US2020/027921, mailed on Jul. 24, 2020, 16 pages.

Nakayama, Yasuhide. Microporous Stent Achieves Brain Aneurysm Occlusion Without Disturbing Branching Flow. NeuroNews Nov. 2012; 8:1-2.

Nishi S, Nakayama Y, Ishibashi-Ueda FI, Okamoto Y, Yoshida M. Development of microporous self-expanding stent grafts for treating

(56) References Cited

OTHER PUBLICATIONS cerebral aneurysms: designing micropores to control intimal hyperplasia. J Artif Organs 2011; 14:348-356.
Clough, Norman E. Introducing a New Family of GORE ePTFE Fibers (2007), pp. 1-10.
English translation of RU2434604 (C1), filed Apr. 30, 2010, translation powered by EPO and Google, 8 pages.
EPO Form 1002 for EP16196687.4 Filed Dec. 28, 2016.
International Search Report and Written Opinion received for PCT Patent Application No. PCT/US2018/050779, mailed on Dec. 7, 2018, 14 pages.
Mano Thubrikar, "The Aortic Valve", Chapter 1: Geometry of the Aortic Valve, CRC Press, Inc., Informa Healthcare, 5 2011, 40 pages.
Norman E. Clough. Introducing a New Family of GORE (Trademark) ePTFE Fibers (2007).
Opposition from EP16196687.4, mailed on Dec. 12, 2019, 38 pages.
Opposition from EP17187595.8, filed Sep. 12, 2019, 50 pages.

\* cited by examiner

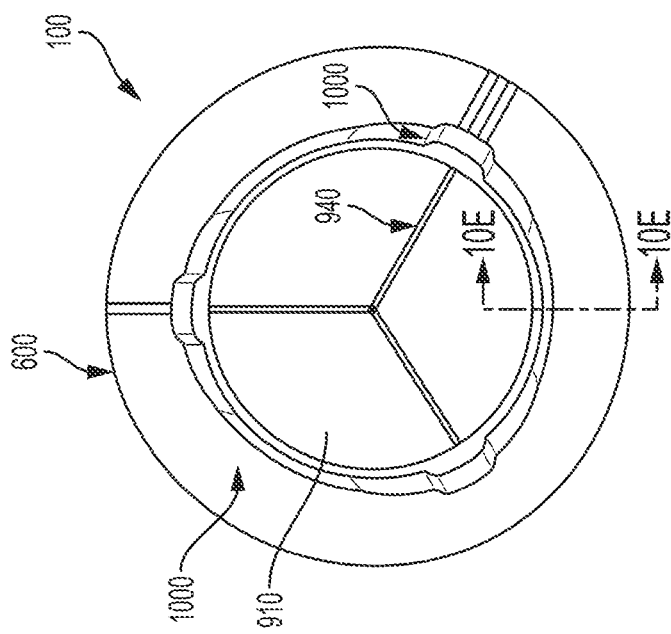
FIG. 10C
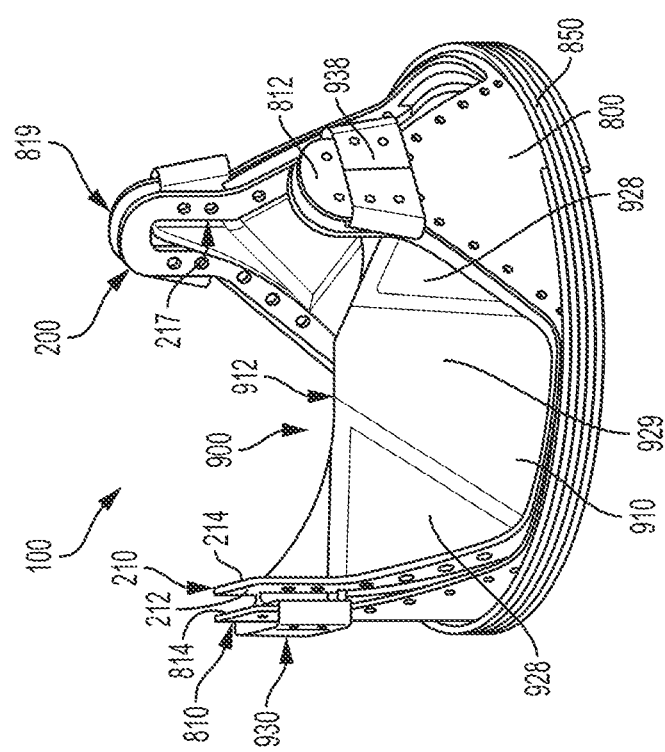
FIG. 10A
FIG. 10B

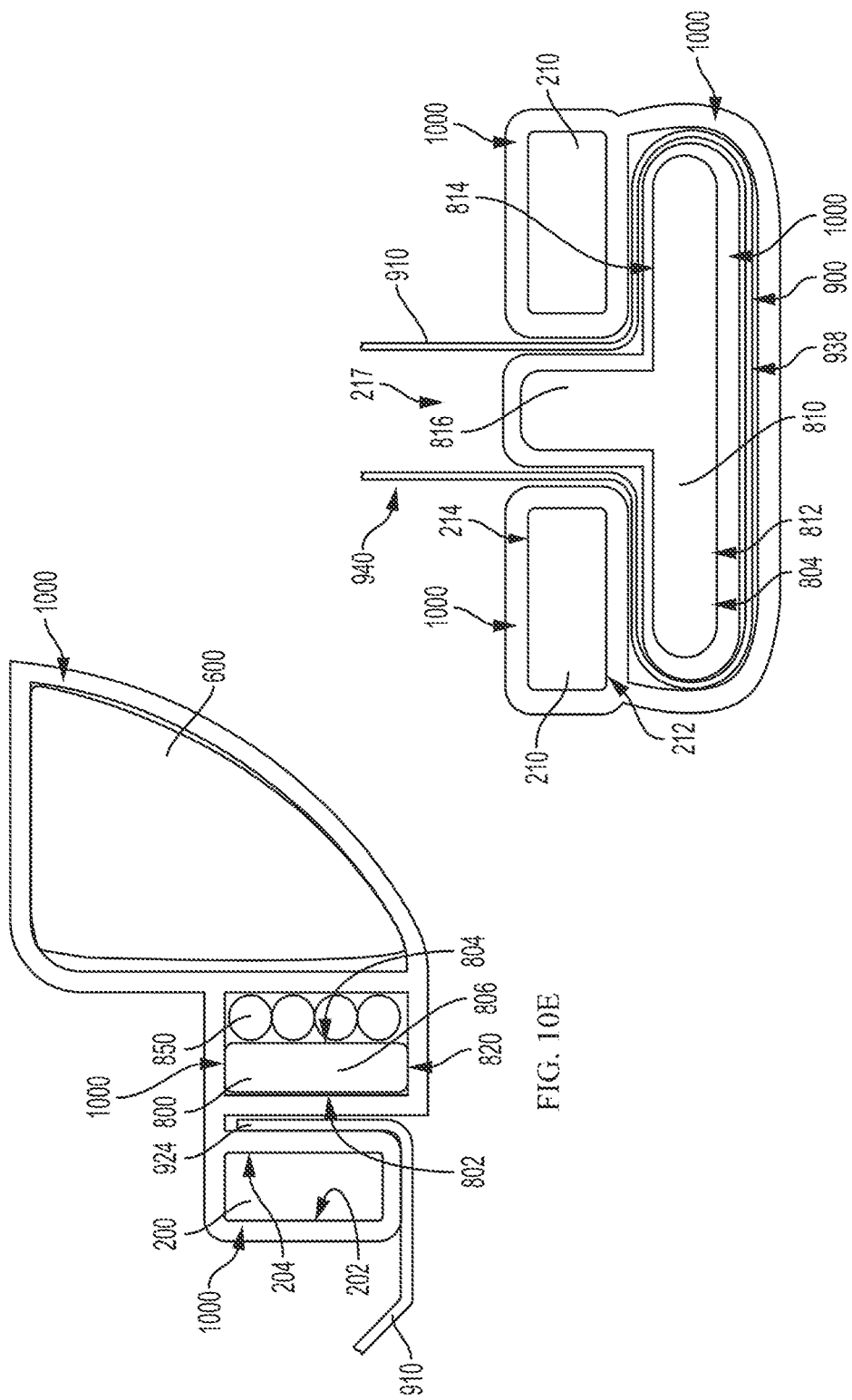

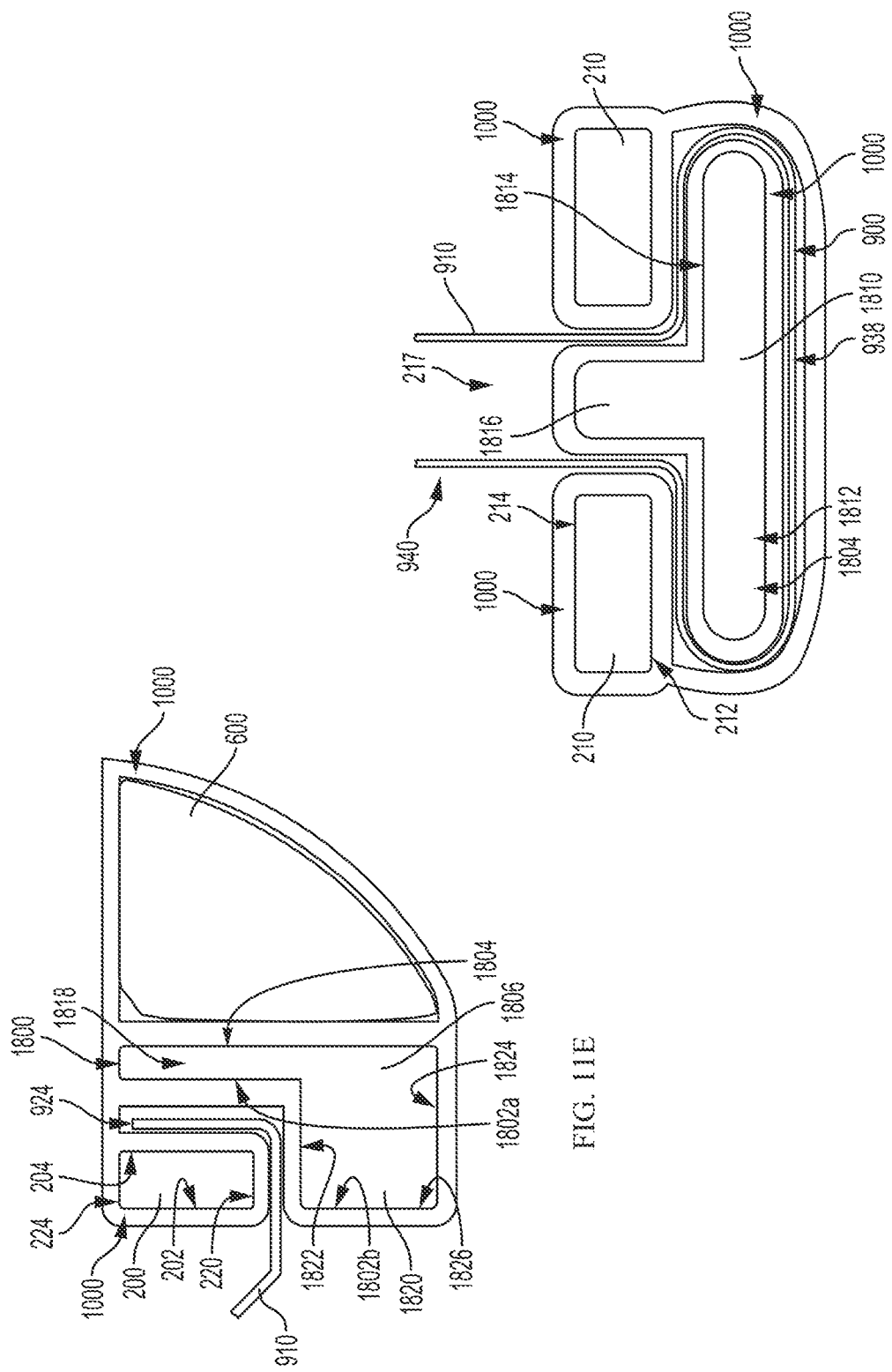

PROSTHETIC HEART VALVE

CROSS-REFERENCE TO RELATED APPLICATION

This application is a continuation of U.S. application Ser. No. 16/129,685, filed Sep. 12, 2018, which claims the benefit of Provisional Application No. 62/579,763, filed Oct. 31, 2017, both of which are incorporated herein by reference in its entireties.

FIELD

The present disclosure relates generally to prosthetic valves and more specifically flexible leaflet-type prosthetic heart valve devices.

BACKGROUND

A number of fabrication techniques have been used to couple the leaflets to a frame, including sewing individual leaflets to the frame (biological and synthetic), and for synthetic leaflets only, injection molding and dip coating a polymer onto the frame. In many cases, the resulting leaflet is supported on the frame and defines a flap having a mounting edge where the leaflet is coupled to the frame and a free edge that allows the flap to move. The flap moves under the influence of fluid pressure. In operation, the leaflets open when the inflow fluid pressure exceeds the outflow fluid pressure and closes when the outflow fluid pressure exceeds the inflow fluid pressure. The free edges of the leaflets coapt under the influence of outflow fluid pressure, closing the valve to prevent downstream blood from flowing retrograde through the valve.

Valve durability under the repetitive loads of the leaflets opening and closing is dependent, in part, on the load distribution between the leaflet and the frame. Further, substantial load is encountered on the leaflet when in the closed position. Mechanical failure of the leaflet can arise, for example, at the mounting edge, where the flexible leaflet is supported by the relatively rigid frame, particularly at the commissure posts. The repetitive loads of leaflet opening and closing leads to material failure by fatigue, creep or other mechanism, depending in part on the leaflet material. Mechanical failure at the mounting edge is especially prevalent with synthetic leaflets.

There remains a need for a more durable flexible leaflet prosthetic valve.

SUMMARY

According to one example, ("Example 1"), a prosthetic valve includes a leaflet frame that defines a cylinder and includes a leaflet frame inner side, a leaflet frame outer side, and a leaflet frame inflow edge. The leaflet frame further includes a leaflet frame central axis and a plurality of leaflet frame commissure posts extending along the leaflet frame central axis, wherein each leaflet frame commissure post defines a post slot therethrough such that the leaflet frame includes a plurality of post slots. The prosthetic valve further includes a leaflet construct comprising a plurality of leaflets and a bridge region situated between adjacently situated leaflets, wherein each bridge defines a bridge loop such that the leaflet construct defines a plurality of bridge loops, and wherein each bridge loop is situated adjacent to the leaflet frame outer side such that the leaflet construct extends through the plurality of post slots. The leaflet frame further includes an outer frame having a plurality of outer frame commissure posts, wherein each outer frame commissure post is disposed within a bridge loop of the plurality of bridge loops. The outer frame further includes an outer frame inner side, an outer frame outer side, an outer frame inflow edge, and an annular shoulder, wherein the annular shoulder has a shoulder surface situated opposite the outer frame inflow edge. The leaflet frame is received with an interior region defined by the outer frame such that the leaflet construct is positioned between the outer frame inner side and the leaflet frame outer side, and such that the leaflet construct is positioned between the leaflet frame inflow edge and the shoulder surface of the outer frame.

According to another example, ("Example 2") further to Example 1, the outer frame commissure posts include commissure post tips and the leaflet frame is positioned between the outer frame commissure post tips and the shoulder surface of the annular shoulder.

According to another example, ("Example 3") further to any of the preceding Examples, the outer frame inner side includes a first surface and a second surface radially offset from the first surface such that the first surface has a first diameter that is larger than a second diameter of the second surface, wherein a diameter of the leaflet frame outer side is less than the first diameter of the first surface of the outer frame inner side and greater than the second diameter of the second surface of the outer frame inner side.

According to another example, ("Example 4") further to any of the preceding Examples, the leaflet frame is supported by the annular shoulder of the outer frame.

According to another example, ("Example 5") further to any of the preceding Examples, each of the leaflets includes a fold-over portion, wherein the fold-over portion of each of the leaflets is folded around the inflow edge of the leaflet frame to the outside surface of the leaflet frame.

According to another example, ("Example 6") further to any of the preceding Examples, the leaflet frame is coupled to the outer frame.

According to another example, ("Example 7") further to Example 6, the leaflet frame, the outer frame, and the leaflet construct each include a plurality of corresponding apertures, wherein the leaflet frame and the outer frame are coupled together by a securement structure that passes through adjacent apertures of the leaflet frame, outer frame, and leaflet construct and is operable to couple the outer frame to the leaflet frame.

According to another example, ("Example 8") further to any of the preceding Examples, the securement structure is suture.

According to another example, ("Example 9") further to any of the preceding Examples the prosthetic valve further includes a sewing cuff coupled to the outer frame.

According to another example, ("Example 10") further to any of the preceding Examples, the leaflet construct comprises an ePTFE composite.

According to another example, ("Example 11") further to Example 9, the ePTFE composite comprises perfluoromethyl vinyl ether and tetrafluoroethylene.

According to another example, ("Example 12") a prosthetic valve includes a leaflet frame defining a cylinder and including a leaflet frame inner side, a leaflet frame outer side, and a leaflet frame inflow edge, the leaflet frame further including a leaflet frame central axis and a plurality of leaflet frame commissure posts extending along the leaflet frame central axis, each leaflet frame commissure post defining a post slot therethrough such that the leaflet frame includes a plurality of post slots; a leaflet construct comprising a plurality of leaflets and a bridge region situated between adjacently situated leaflets, each bridge defining a bridge loop such that the leaflet construct defines a plurality of bridge loops, each bridge loop being situated adjacent to the leaflet frame outer side such that the leaflet construct extends through the plurality of post slots; and an outer frame including a plurality of outer frame commissure posts, each outer frame commissure post being disposed within a first bridge loop of the plurality of bridge loops, the outer frame further including an outer frame inner side, an outer frame outer side, an outer frame inflow edge, the leaflet frame being received with an interior region defined by the outer frame such that the leaflet construct is positioned between the outer frame inner side and the leaflet frame outer side, and such that the leaflet construct extends along the leaflet frame inflow edge.

According to another example, ("Example 13") further to Example 12, each of the leaflets includes a fold-over portion, and wherein the fold-over portion of each of the leaflets is folded around the inflow edge of the leaflet frame to the outside surface of the leaflet frame.

According to another example, ("Example 14") further to any of Examples 12 to 13, the leaflet frame, the outer frame, and the leaflet construct each include a plurality of corresponding apertures, and wherein the leaflet frame and the outer frame are coupled together by a securement structure that passes through adjacent apertures of the leaflet frame, outer frame, and leaflet construct and is operable to couple the outer frame to the leaflet frame.

According to another example, ("Example 15") further to Example 14, the securement structure is suture.

According to another example, ("Example 16") a method of making a prosthetic valve includes providing a leaflet construct including a plurality of leaflets and a bridge region situated between adjacently situated leaflets, wherein each leaflet includes a leaflet fold-over region. The method further includes providing an outer frame including a plurality of outer frame commissure posts, wherein the outer frame further includes an outer frame inner side, an outer frame outer side, an outer frame inflow edge, and an annular shoulder, wherein the annular shoulder has a shoulder surface situated opposite the outer frame inflow edge. The method further includes folding each of the bridge regions into a bridge loop and disposing each bridge loop about a corresponding outer frame commissure post of the outer frame such that each outer frame commissure post is disposed within a bridge loop of the plurality of bridge loops. The method further includes securing the fold-over regions of the leaflets to the outer frame inner side such that the fold-over regions of the leaflets adopt a first profile, and providing a leaflet frame including an inner side, an outer side, and an inflow edge extending between the inner side and the outer side, wherein the leaflet frame further includes a plurality of leaflet frame commissure posts that correspond with the outer frame commissure posts, wherein each leaflet frame commissure post defining a post slot. The method further includes disposing the leaflet frame within an interior region defined by the outer frame such that adjacently situated leaflets of the leaflet construct extend through the post slots of the leaflet frame commissure posts, and securing the leaflet frame to the outer frame such that the leaflet frame inflow edge of the leaflet frame causes the fold-over regions of the leaflets to adopt a second different profile, and such that the fold-over region of each leaflet of the plurality of leaflets is positioned between the outer frame inner side and the leaflet frame outer side, and such that the leaflet construct is positioned between the leaflet frame inflow edge and the shoulder surface of the outer frame.

According to another example, ("Example 17") further to Example 16, the method includes securing the leaflet frame to the outer frame via a securement structure.

According to another example, ("Example 18") further to any of Examples 16 to 17, the method includes securing the leaflet frame to the outer frame by suturing the leaflet frame to the outer frame.

According to another example, ("Example 19") further to Examples 16 to 18, the leaflet frame, the outer frame, and the fold-over regions of the leaflets each include a plurality of apertures, wherein method further includes aligning corresponding apertures of the leaflet frame, the outer frame, and the fold-over regions of the leaflet and passing the securement structure through adjacent apertures.

According to another example, ("Example 20") further to any of Examples 16 to 19, the leaflet frame is secured to the outer frame such that the fold-over portion of each of the leaflets is folded around the inflow edge of the leaflet frame to the outside surface of the leaflet frame.

According to another example, ("Example 21") a method of treating a failing natural heart valve includes surgically implanting a prosthetic valve in accordance with any of examples 1 to 15.

While multiple embodiments are disclosed, still other embodiments will become apparent to those skilled in the art from the following detailed description, which shows and describes illustrative embodiments. Accordingly, the drawings and detailed description are to be regarded as illustrative in nature and not restrictive.

BRIEF DESCRIPTION OF THE DRAWINGS

The accompanying drawings are included to provide a further understanding of the present disclosure and are incorporated in and constitute a part of this specification, illustrate embodiments described herein, and together with the description serve to explain the principles discussed in this disclosure.

FIG. 10A is an outflow side perspective view of a prosthetic heart valve, according to some embodiments;

FIG. 10B is a side view of the prosthetic heart valve of FIG. 10A, according to some embodiments;

FIG. 10C is a top view of the outflow side of the prosthetic heart valve of FIG. 10A, according to some embodiments;

FIG. 10D is cross section view of the prosthetic heart valve of FIG. 10B taken along line 10D-10D;

FIG. 10E is cross section view of the prosthetic heart valve of FIG. 10C taken along line 10E-10E;

FIG. 11D is cross section view of the prosthetic heart valve of FIG. 11B taken along line 11D-11D;

FIG. 11E is cross section view of the prosthetic heart valve of FIG. 11C taken along line 11E-11E.

DETAILED DESCRIPTION

Figure 1A:
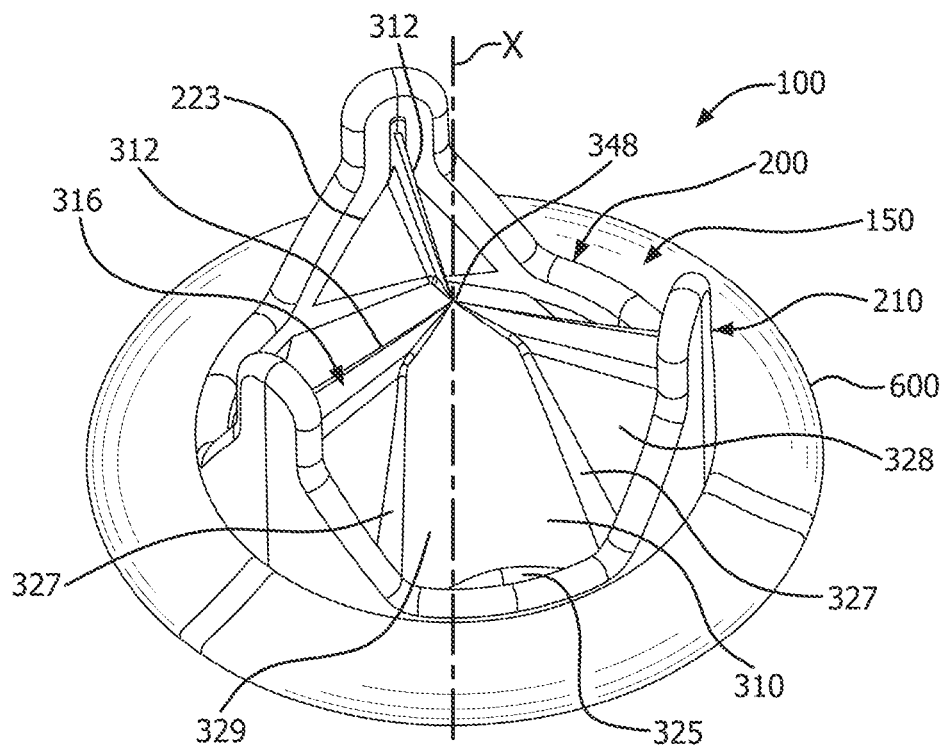
FIG. 1A is an outflow side perspective view of a prosthetic heart valve in accordance with an embodiment.

Persons skilled in the art will readily appreciate that various aspects of the present disclosure can be realized by any number of methods and apparatus configured to perform the intended functions. Stated differently, other methods and apparatus can be incorporated herein to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Although the embodiments herein may be described in connection with various principles and beliefs, the described embodiments should not be bound by theory. For example, embodiments are described herein in connection with prosthetic valves, more specifically cardiac prosthetic valves. However, embodiments within the scope of this disclosure can be applied toward any valve or mechanism of similar structure and/or function, including for example venous, arterial, aortic, and mitral valves. Furthermore, embodiments within the scope of this disclosure can be applied in non-cardiac applications.

The term leaflet as used herein in the context of prosthetic valves is a flexible component of a one-way valve wherein the leaflet is operable to move between an open and closed position under the influence of a pressure differential. In an open position, the leaflet allows blood to flow through the valve. In a closed position, the leaflet substantially blocks retrograde flow through the valve. In embodiments comprising multiple leaflets, each leaflet cooperates with at least one neighboring leaflet to block the retrograde flow of blood. The pressure differential in the blood is caused, for example, by the contraction of a ventricle or atrium of the heart, such pressure differential typically resulting from a fluid pressure building up on one side of the leaflets when closed. As the pressure on an inflow side of the valve rises above the pressure on the outflow side of the valve, the leaflets open and blood flows therethrough. As blood flows through the valve into a neighboring chamber or blood vessel, the pressure on the inflow side equalizes with the pressure on the outflow side. As the pressure on the outflow side of the valve raises above the blood pressure on the inflow side of the valve, the leaflet returns to the closed position generally preventing retrograde flow of blood through the valve.

The term membrane as used herein refers to a sheet comprising a single material, such as, but not limited to, expanded fluoropolymer. The term biocompatible material as used herein generically refers to any material with biocompatible characteristics including synthetic, such as, but not limited to, a biocompatible polymer, or a biological material, such as, but not limited to, bovine pericardium.

The terms native valve orifice and tissue orifice refer to an anatomical structure into which a prosthetic valve can be placed. Such anatomical structure includes, but is not limited to, a location wherein a cardiac valve may or may not have been surgically removed. It is understood that other anatomical structures that can receive a prosthetic valve include, but are not limited to, veins, arteries, ducts and shunts. It is further understood that a valve orifice or implant site may also refer to a location in a synthetic or biological conduit that may receive a valve.

As used herein, "couple" means to join, connect, attach, adhere, affix, or bond, whether directly or indirectly, and whether permanently or temporarily.

Embodiments herein include various apparatus, systems, and methods for a prosthetic valve, such as, but not limited to, cardiac valve replacement. The valve is operable as a one-way valve wherein the valve defines a valve orifice into which leaflets open to permit flow and close so as to occlude the valve orifice and prevent flow in response to differential fluid pressure.

Figure 1B:
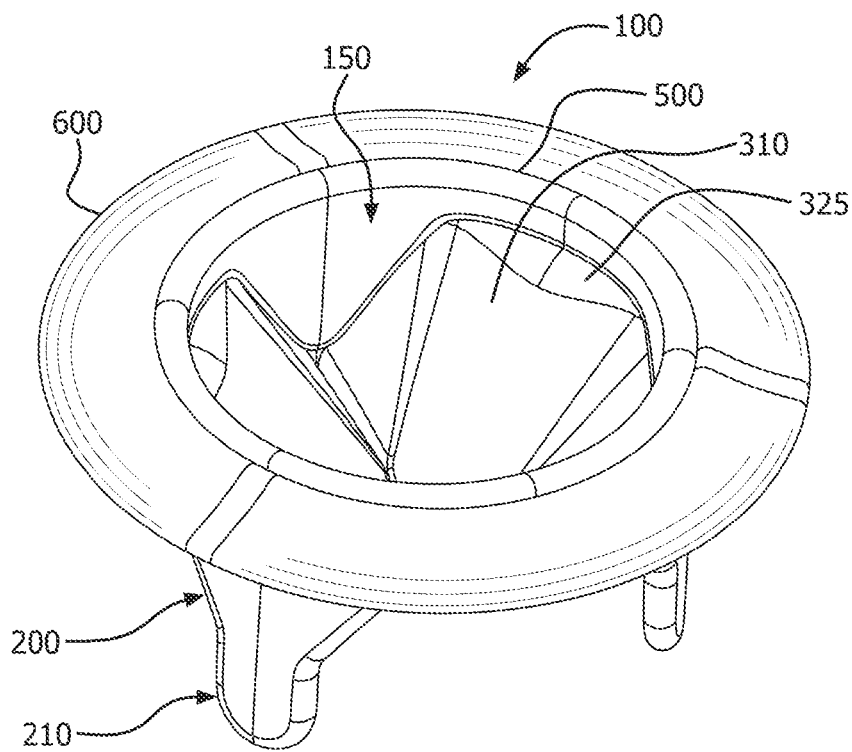
FIG. 1B is an inflow side perspective view of the embodiment of the valve of FIG. 1A.

FIGS. 1A and 1B are outflow and inflow, respectfully, perspective views of a valve 100 in the form of a prosthetic heart valve, in accordance with an embodiment. The components of the valve 100 that are visible in FIGS. 1A and 1B include three flexible leaflets 310, a leaflet frame 200 including three commissure posts 210 that has been covered with various material, a base frame 500 that has been covered with various material, and a sewing cuff (or suture cuff) 600. In some examples, the leaflet free edges 312 of the leaflets 310 come together at a coaptation region 316 in a Y-shaped pattern (when viewed from above) to close the valve 100. In some other examples, the leaflets 310 additionally or alternatively come together at a coaptation region at the triple point 348. The valve 100 closes in this fashion when the pressure of the blood on the outflow side (as viewed in FIG. 1A) is greater than the pressure of the blood on the inflow side of the valve (as viewed in FIG. 1B). The leaflet free edges 312 of the leaflets 310 move apart to open the valve 100 and to let blood flow through the valve 100 from the inflow side as viewed in FIG. 1B when the pressure of the blood on the inflow side of the valve 100 is greater than the pressure on the outflow side of the valve 100.

FIGS. 2-5B show various components that are included in the valve 100, in accordance with an embodiment.

Figure 2:
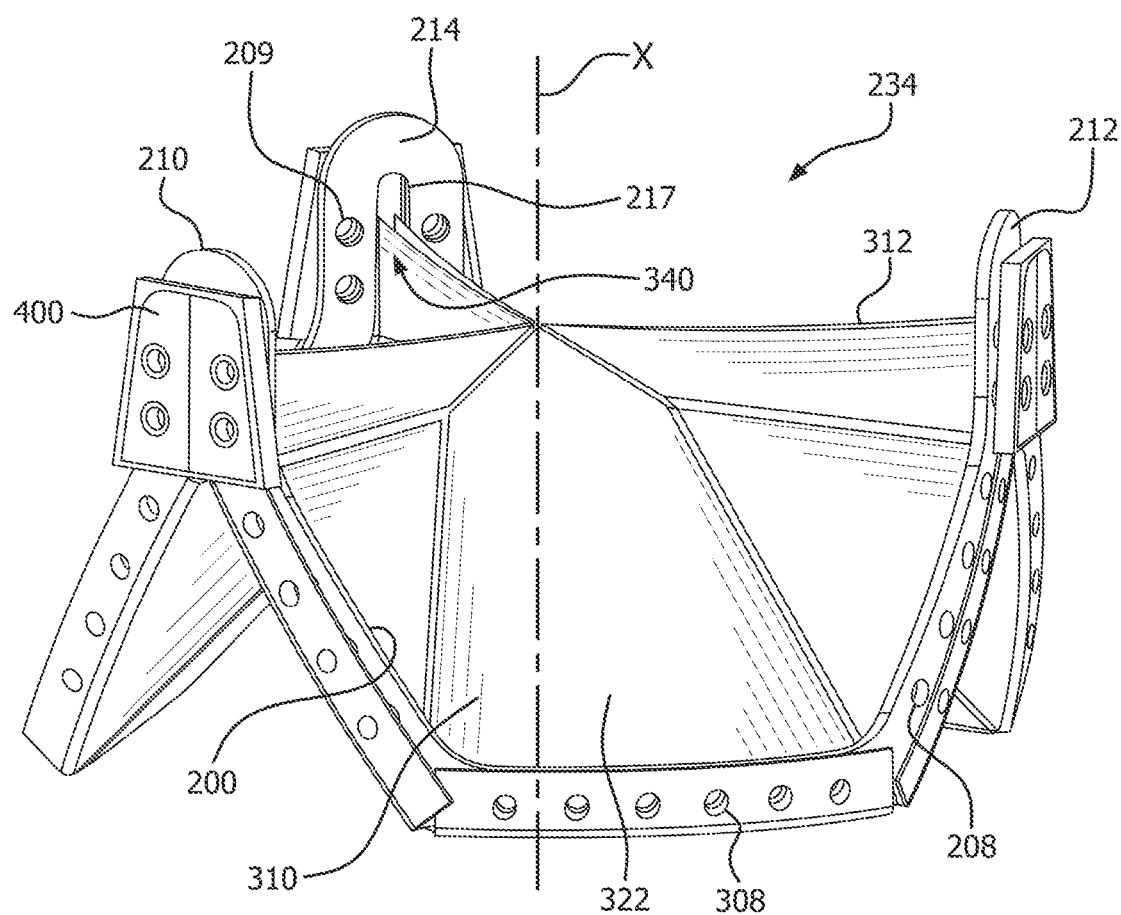
FIG. 2 is a perspective view of a leaflet frame assembly of the embodiment of the valve of FIG. 1A.
Figure 3:
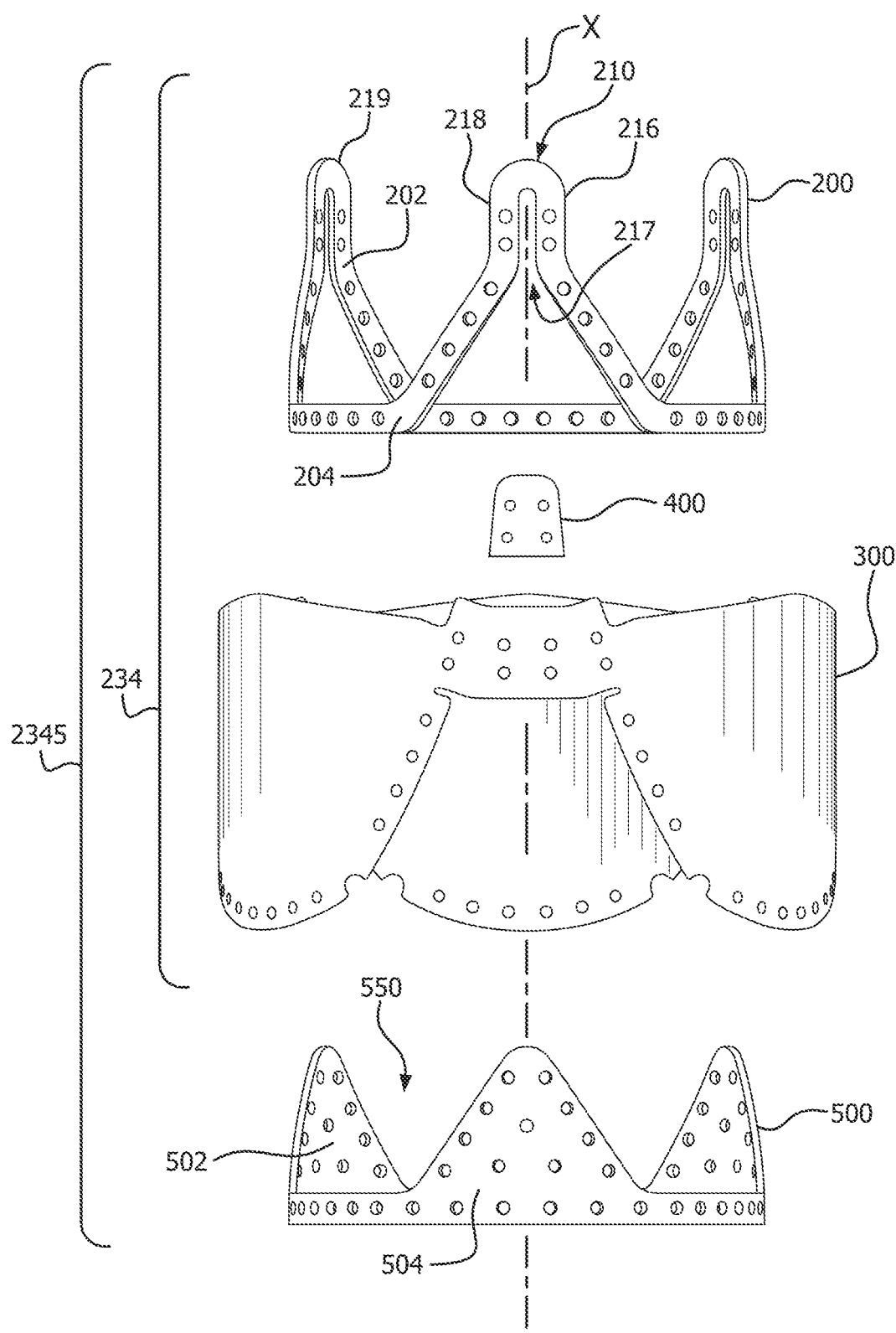
FIG. 3 is a side exploded view of the leaflet frame, retention element, leaflet construct and base frame, of an embodiment of a valve.
Figure 4:
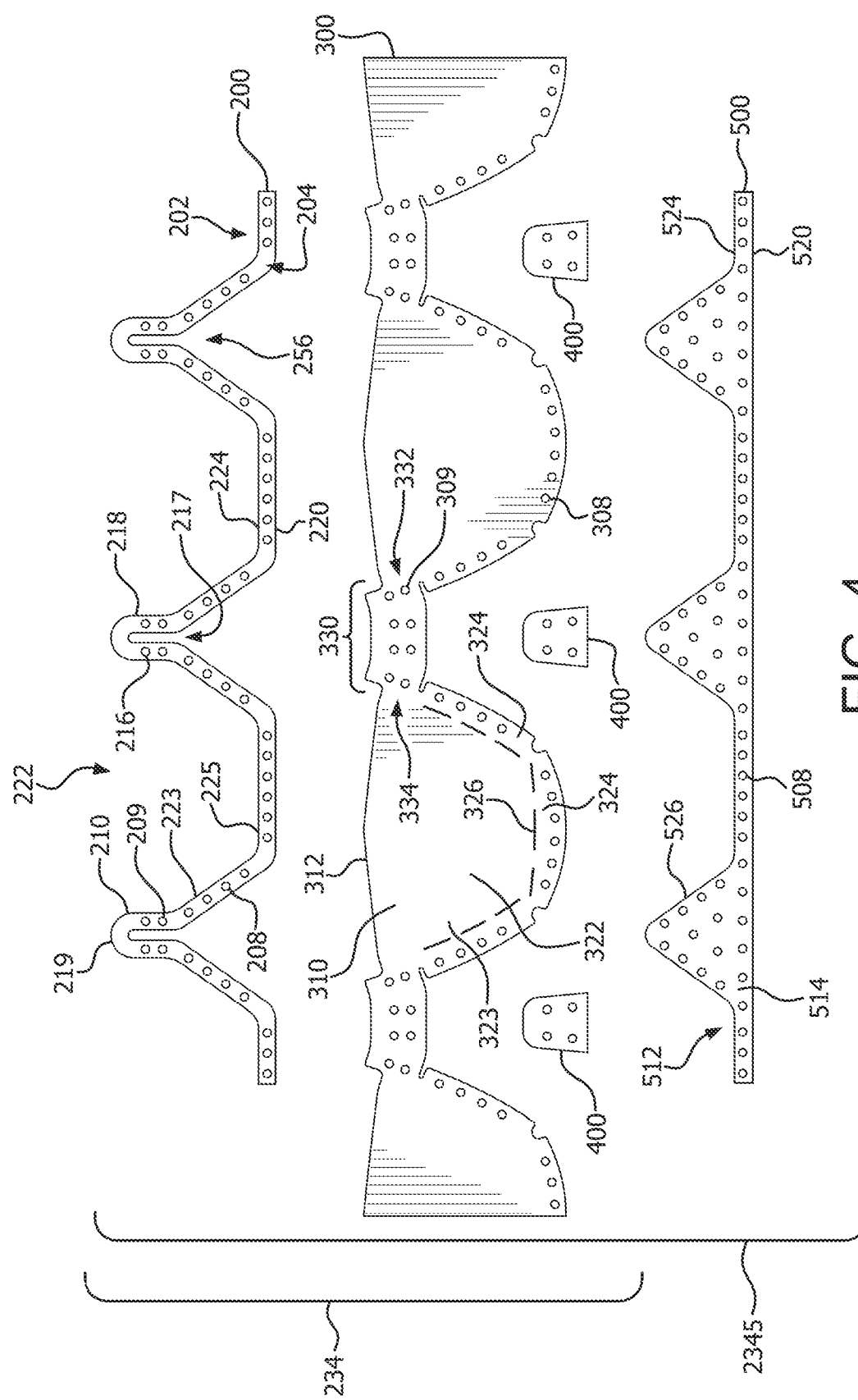
FIG. 4 is a representation of the embodiment of the valve of FIG. 3 unrolled to a flat orientation, in accordance with an embodiment.
Figure 5B:
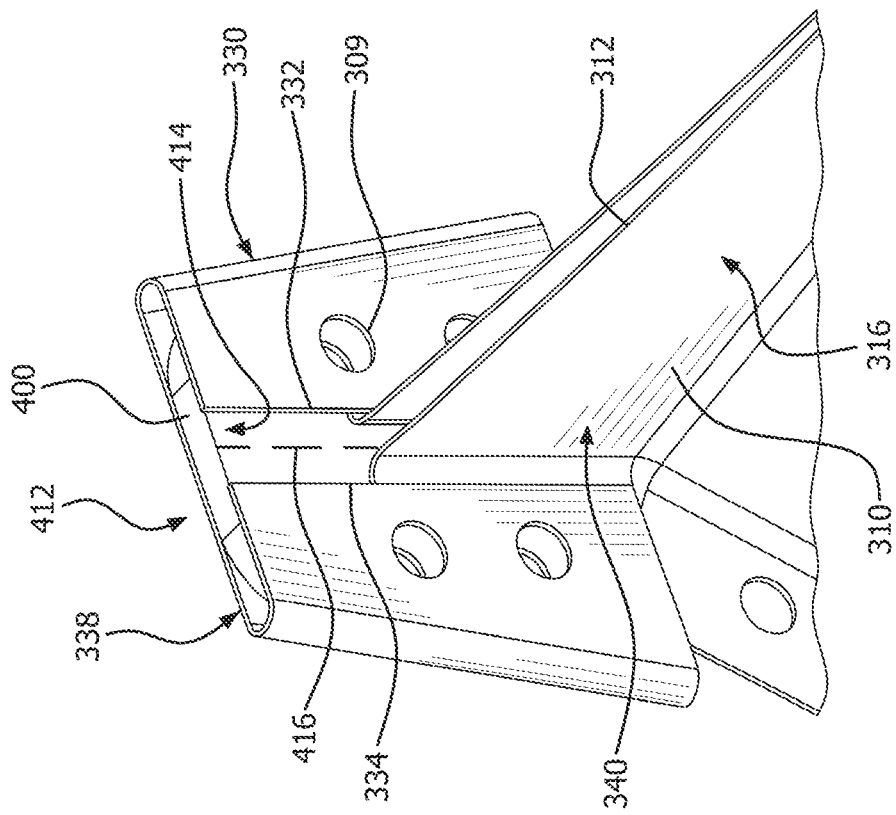
FIG. 5B is a perspective view of the bridge region formed into a bridge loop and containing a retention element, in accordance with the embodiment of FIG. 2.
Figure 5A:
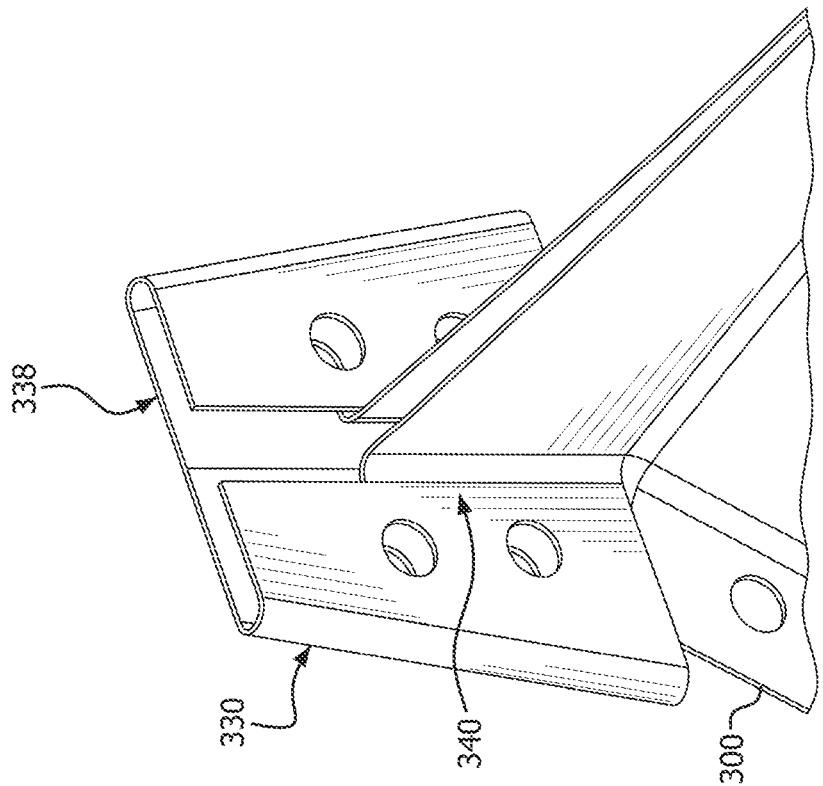
FIG. 5A is a perspective view of the bridge region formed into a bridge loop, in accordance with the embodiment of FIG. 2.

FIG. 2 is a perspective view of a leaflet frame assembly 234, in accordance with an embodiment, also shown in FIG. 3 in an exploded view and shown in FIG. 4 in an exploded view wherein the annular components have been longitudinally cut and laid open, so as to better illustrate the elements of the valve components. The leaflet frame assembly 234 comprises a leaflet frame 200, a leaflet construct 300, and a plurality of retention elements 400.

Leaflet Frame

The leaflet frame 200 is operable to hold and support the leaflet construct 300. The leaflet frame 200 is annular, that is it defines a cylinder having an axis X and a plurality of commissure posts 210 extending generally along the axis x. In some examples, the plurality of commissure posts 210 extend parallel to the axis x. In some examples, the plurality of commissure posts 210 are spaced from one another. In some examples, the commissure posts are evenly distributed about the leaflet frame 200. In various embodiments, each commissure post 210 defines a post slot 217 therethrough that is aligned parallel to the axis X. Between the commissure posts 210 is a leaflet window 222 that is operable to couple to and support the leaflet 310 around the perimeter of the leaflet 310 except for the leaflet free edge 312.

The leaflet frame 200 defines a cylinder having a leaflet frame inner side 202 and a leaflet frame outer side 204 opposite the leaflet frame inner side 202. The leaflet frame 200 further defines a plurality of commissure posts 210. Each commissure post 210 has a post outer side 212 and a post inner side 214 opposite the post outer side 212. The commissure post 210 is defined by a first post leg 216 and a second post leg 218 separated by a post slot 217 therebetween. A commissure tip 219 couples the first post leg 216 and the second post leg 218.

In accordance with an embodiment, the leaflet frame 200 is annular about a central longitudinal axis X of the valve 100 as shown in FIGS. 2 and 3. The leaflet frame 200 defines a plurality of leaflet windows 222 that follow the shape of the leaflet 310. In accordance with an embodiment, each of the leaflet windows 222 includes two leaflet window sides 223 and a leaflet window base 225, defining three sides of an isosceles trapezoid, wherein the leaflet window base 225 is substantially flat. The leaflet base 325 is coupled to the leaflet window base 225 and each of the two leaflet sides 323 are coupled to one of the two leaflet window sides 223. The adjacent leaflet window sides 223 are interconnected by a commissure post 210 comprising of a first post leg 216 and a second post leg 218 that extend from adjacent leaflet window sides 223 and meet at a commissure tip 219. The commissure posts 210 are equally spaced (or evenly distributed) from one another around the leaflet frame 200, though an even distribution is not required. The first post leg 216 and the second post leg 218 define a post slot 217 therebetween.

The leaflet frame 200 can be etched, cut, laser cut, stamped, three-dimensional printed, among other suitable processes, into an annular structure or a sheet of material, with the sheet then formed into an annular structure.

The leaflet frame 200 can comprise, such as, but not limited to, any elastically deformable metallic or polymeric material that is generally biocompatible. The leaflet frame 200 can comprise a shape-memory material, such as nitinol, a nickel-titanium alloy. Other materials suitable for the leaflet frame 200 include, but not limited to, other titanium alloys, stainless steel, cobalt-nickel alloy, polypropylene, acetyl homopolymer, acetyl copolymer, other alloys or polymers, or any other material that is generally biocompatible having adequate physical and mechanical properties to function as a leaflet frame 200 as described herein.

Leaflet Construct

The leaflet construct 300 is that portion of the valve 100 that comprises the leaflets 310 and the structure for coupling the leaflets 310 to the leaflet frame 200. In accordance with an embodiment, the leaflet construct 300 defines a contiguous annular ring defining a plurality of leaflets 310 and a bridge region 330 between each of the leaflets 310. As used herein, contiguous means without a break or a seam, that is, seam less. Each bridge region defines a bridge first end 332 adjacent a first leaflet 310 and a bridge second end 334 adjacent a second leaflet 310. The leaflets extend radially inward from the leaflet frame 200 when coupled to the leaflet frame 200. Each of the leaflets 310 define a fold-over portion 324 that is folded over and lies against a leaflet frame outer side 204 of the leaflet frame 200 and coupled thereto. Each of the bridge regions 330 defines a bridge loop 338 with a coaptation neck 340 between the bridge loop 338 and the adjacent leaflets 310. The coaptation neck 340 is operable to pass through one of the post slots 217 so that the bridge loop 338 is adjacent to the outer portion of the leaflet frame 200 and the leaflets 310 extend radially inward from the leaflet frame 200.

The leaflet construct 300 comprising the flexible leaflets 310 can be made of polymer. For example, pre-shaped polymer leaflets can be made by starting from a cylinder of polymer material that has been cut into a shape like that shown in FIGS. 3 and 4.

The leaflet construct 300 can also be made from a sheet of polymer material that has been cut into a shape like that shown in FIGS. 3 and 4 and subsequently coupled together into an annular shape. A leaflet construct 300 having a seam, though may not have the advantages of a contiguous, seamless construct that may exhibit a higher tensile strength characteristics. The advantages provided by the retention element 400 may still be realized.

Another way that the leaflet construct 300 may be formed (assuming the use of a material for the leaflets that is suitable for formation in this way) is by compression or injection molding.

In accordance with an embodiment as shown in FIG. 1A, each leaflet 310, at the folds 326, has substantially the shape of an isosceles trapezoid having two leaflet sides 323, a leaflet base 325 and a leaflet free edge 312 opposite the leaflet base 325, corresponding to the two leaflet window sides 223 and a leaflet window base 225. The two leaflet sides 323 diverge from the leaflet base 325, wherein the leaflet base 325 is substantially flat.

In accordance with other embodiments of the valve 100 as shown in FIG. 1A, each leaflet 310 includes a central region 329 and two side regions 328 on opposite sides of the central region 329. The central region 329 is defined by a shape substantially that of an isosceles trapezoid defined by two central region sides 327, the leaflet base 325 and the leaflet free edge 312. Each of the side regions 328 has a shape substantially that of a triangle and each are defined by one of the central region sides 327, one of the leaflet sides 323, and the leaflet free edge 312.

In accordance with another embodiment, the leaflet window may be described as having a U-shape (e.g., a parabolic shape). The leaflet frame generally defines a plurality of U-shaped portions as one proceeds annularly around the leaflet frame, defining a plurality of commissure posts and a plurality of leaflet window frame portions.

As shown in FIG. 4, each of the leaflets 310 has a leaflet belly portion 322, and a fold-over portion 324. The leaflet belly portion 322 of each leaflet 310 is the operating portion of the leaflet 310 when in a finished and implanted valve 100. The fold-over portion 324 of each leaflet 310 is the portion that is used to secure the leaflet 310 to the two leaflet window sides 223 and the leaflet window base 225 of the leaflet frame 200. Each leaflet window side 223 and a leaflet window base 225 of the leaflet frame 200 fits into a fold 326 that is formed between the leaflet belly portion 322 and the fold-over portion 324 of a respective one of the leaflet sides 323 and leaflet base 325, respectively, of the leaflets 310, as shown in FIG. 2. The leaflet belly portion 322 of each leaflet 310 includes enough material between the commissure posts 210 of the leaflet frame 200 so that the leaflet free edge 312 of the three leaflet belly portions 322 can come together or coapt in the interior of the valve 100 to close the valve 100 as shown in FIG. 1.

Figure 6:
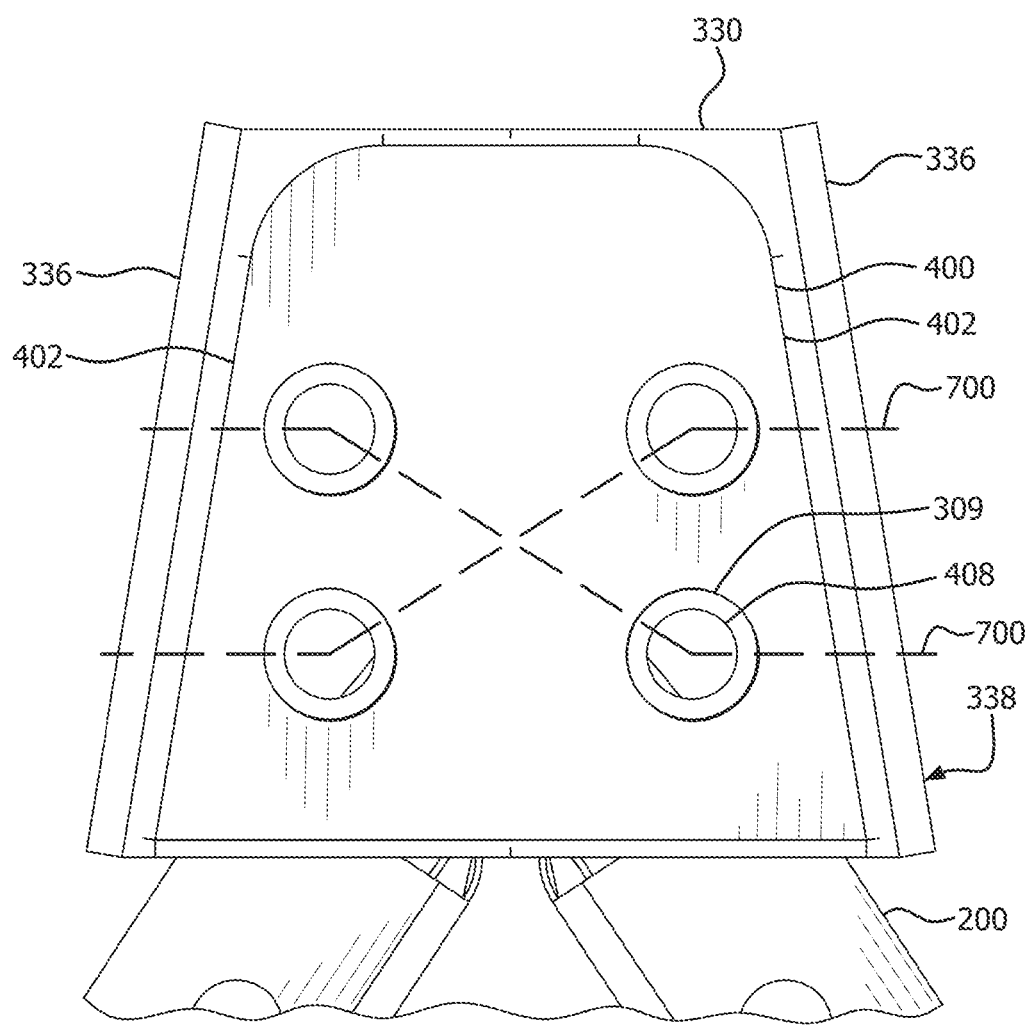
FIG. 6 is a front view of the bridge region of the embodiment of FIG. 7.

Between each of the leaflets 310 is a bridge region 330, as shown in FIGS. 4, 5A, 5B and 8. The bridge region 330 is operable to be formed into a bridge loop 338 having a generally rectangular shape, folding about two loop fold lines 336 so as to contain the retention element 400 therein as discussed below, as shown in FIGS. 5A, 5B, 6 and 8. Due to the curvature of the annular leaflet frame 200, the two loop fold lines 336 form an angle alpha, which corresponds to the retention element sides 402 as shown in FIG. 6, in accordance with an embodiment.

In accordance with an embodiment, the leaflet construct 300 can comprise a biocompatible material that is not of a biological source and that is sufficiently compliant and strong for the particular purpose, such as a biocompatible polymer. In an embodiment, the leaflet construct 300 comprises a membrane that is combined with an elastomer, or elastomeric material, or a non-elastomeric material to form a composite material. In accordance with other embodiments, the biocompatible material that makes up the leaflet construct 300 comprises a biological material, such as, but not limited to, bovine or porcine sourced material.

The shape of the leaflets 310 are defined in part by the shape of the leaflet frame 200 and the leaflet free edge 312. The shape of the leaflets 310 can also be defined by the structures and processes used to manufacture the valve 100, such as, but not limited, those described below. For example, in accordance with an embodiment, the shape of the leaflets 310 also depends in part on molding the leaflets 310 using molding and trimming processes to impart a predetermined shape to the leaflet 310.

The leaflets 310 generally flex about the leaflet base 325 about the leaflet window base 225 of the U-shaped portion as the leaflets 310 open and close. In an embodiment, when the valve 100 is closed, generally about half of each leaflet free edge 312 abuts an adjacent half of a leaflet free edge 312 of an adjacent leaflet 310, as shown in FIG. 1A. The three leaflets 310 of the embodiment of FIG. 1A meet at a triple point 348. The valve orifice 150 is occluded when the leaflets 310 are in the closed position stopping fluid flow.

Leaflet Construct Material

The leaflet constructs (e.g., 300) disclosed herein can comprise any biocompatible material sufficiently compliant and flexible, such as a biocompatible polymer (e.g., synthetic) and biological tissue (e.g., of animal origin). For instance, in various examples, the leaflet construct (e.g., 300) is formed of a biocompatible, synthetic material (e.g., including ePTFE and ePTFE composites, or other materials as desired). In accordance with an embodiment, the composite material includes an expanded fluoropolymer material made from porous ePTFE membrane, for instance as generally described in U.S. Pat. No. 7,306,729 to Bacino. In other examples, the construct (e.g., 300) is formed of a natural material, such as repurposed tissue, including bovine tissue, porcine tissue, or the like.

The expandable fluoropolymer, used to form the expanded fluoropolymer material described, can comprise PTFE homopolymer. In some embodiments, blends of PTFE, expandable modified PTFE and/or expanded copolymers of PTFE can be used. Non-limiting examples of suitable fluoropolymer materials are described in, for example, U.S. Pat. No. 5,708,044, to Branca, U.S. Pat. No. 6,541,589, to Baillie, U.S. Pat. No. 7,531,611, to Sabol et al., U.S. patent application Ser. No. 11/906,877, to Ford, and U.S. patent application Ser. No. 12/410,050, to Xu et al. The expanded fluoropolymer membrane can comprise any suitable microstructure, such as pores, for achieving the desired leaflet performance. Other biocompatible polymers that can be suitable for use in the leaflet construct (e.g., 300) include but are not limited to the groups of urethanes, silicones (organopolysiloxanes), copolymers of silicon-urethane, styrene/isobutylene copolymers, polyisobutylene, polyethylene copoly (vinyl acetate), polyester copolymers, nylon copolymers, fluorinated hydrocarbon polymers and copolymers or mixtures of each of the foregoing.

As used herein, the term "elastomer" refers to a polymer or a mixture of polymers that has the ability to be stretched to at least 1.3 times its original length and to retract rapidly to approximately its original length when released. The term "elastomeric material" refers to a polymer or a mixture of polymers that displays stretch and recovery properties similar to an elastomer, although not necessarily to the same degree of stretch and/or recovery. The term "non-elastomeric material" refers to a polymer or a mixture of polymers that displays stretch and recovery properties not similar to either an elastomer or elastomeric material, that is, considered not an elastomer or elastomeric material.

In accordance with some embodiments herein, the leaflet construct (e.g., 300) comprises a composite material having at least one porous synthetic polymer membrane layer having a plurality of pores and/or spaces and an elastomer and/or an elastomeric material and/or a non-elastomeric material filling the pores and/or spaces of the at least one synthetic polymer membrane layer. In accordance with other examples, the leaflet construct (e.g., 300) further comprises a layer of an elastomer and/or an elastomeric material and/or a non-elastomeric material on the composite material. In accordance with examples, the composite material comprises porous synthetic polymer membrane by weight in a range of about 10% to 90%.

An example of a porous synthetic polymer membrane includes expanded fluoropolymer membrane having a node and fibril structure defining the pores and/or spaces. In some examples, the expanded fluoropolymer membrane is expanded polytetrafluoroethylene (ePTFE) membrane. Another example of porous synthetic polymer membrane includes microporous polyethylene membrane.

Examples of an elastomer and/or an elastomeric material and/or a non-elastomeric material include, but are not limited to, copolymers of tetrafluoroethylene and perfluoromethyl vinyl ether (TFE/PMVE copolymer), (per)fluoroalkyl-vinylethers (PAVE), urethanes, silicones (organopolysiloxanes), copolymers of silicon-urethane, styrene/isobutylene copolymers, polyisobutylene, polyethylene-co-poly (vinyl acetate), polyester copolymers, nylon copolymers, fluorinated hydrocarbon polymers and copolymers or mixtures of each of the foregoing. In some examples, the TFE/PMVE copolymer is an elastomer comprising essentially of between 60 and 20 weight percent tetrafluoroethylene and respectively between 40 and 80 weight percent perfluoromethyl vinyl ether. In some examples, the TFE/PMVE copolymer is an elastomeric material comprising essentially of between 67 and 61 weight percent tetrafluoroethylene and respectively between 33 and 39 weight percent perfluoromethyl vinyl ether. In some examples, the TFE/PMVE copolymer is a non-elastomeric material comprising essentially of between 73 and 68 weight percent tetrafluoroethylene and respectively between 27 and 32 weight percent perfluorom ethyl vinyl ether. The TFE and PMVE components of the TFE-PMVE copolymer are presented in wt %. For reference, the wt % of PMVE of 40, 33-39, and 27-32 corresponds to a mol % of 29, 23-28, and 18-22, respectively.

In some examples, the TFE-PMVE copolymer exhibits elastomer, elastomeric, and/or non-elastomeric properties.

In some examples, the composite material further comprises a layer or coating of TFE-PMVE copolymer comprising from about 73 to about 68 weight percent tetrafluoroethylene and respectively from about 27 to about 32 weight percent perfluoromethyl vinyl ether.

In some examples, the leaflet construct is an expanded polytetrafluoroethylene (ePTFE) membrane having been imbibed with TFE-PMVE copolymer comprising from about 60 to about 20 weight percent tetrafluoroethylene and respectively from about 40 to about 80 weight percent perfluoromethyl vinyl ether, the leaflet construct further including a coating of TFE-PMVE copolymer comprising from about 73 to about 68 weight percent tetrafluoroethylene and respectively about 27 to about 32 weight percent perfluorom ethyl vinyl ether on the blood-contacting surfaces.

As discussed above, the elastomer and/or an elastomeric material and/or a non-elastomeric material may be combined with the expanded fluoropolymer membrane such that the elastomer and/or the elastomeric material and/or the non-elastomeric material occupies substantially all of the void space or pores within the expanded fluoropolymer membrane.

Retention Element

The retention element 400 is an element that is operable to be disposed within the bridge loop 338 formed by the bridge region 330 of the leaflet construct 300, which effectively prevents the bridge loop 338 from passing through the post slot 217, and therefore the leaflet construct 300 is mechanically coupled to the commissure post at the post outer side. The retention element 400 has a width that is larger than a width of the post slot 217. With the retention element 400 being disposed in the bridge loop 338, the bridge loop 338 will be prevented from passing through the post slot 217. The size of the bridge loop 338 should correspond closely to the size of the retention element 400 to prevent a portion of the bridge region 330 from extending through the post slot 217 to the valve orifice 150 in case of the suture loosening or failing.

Figure 8:
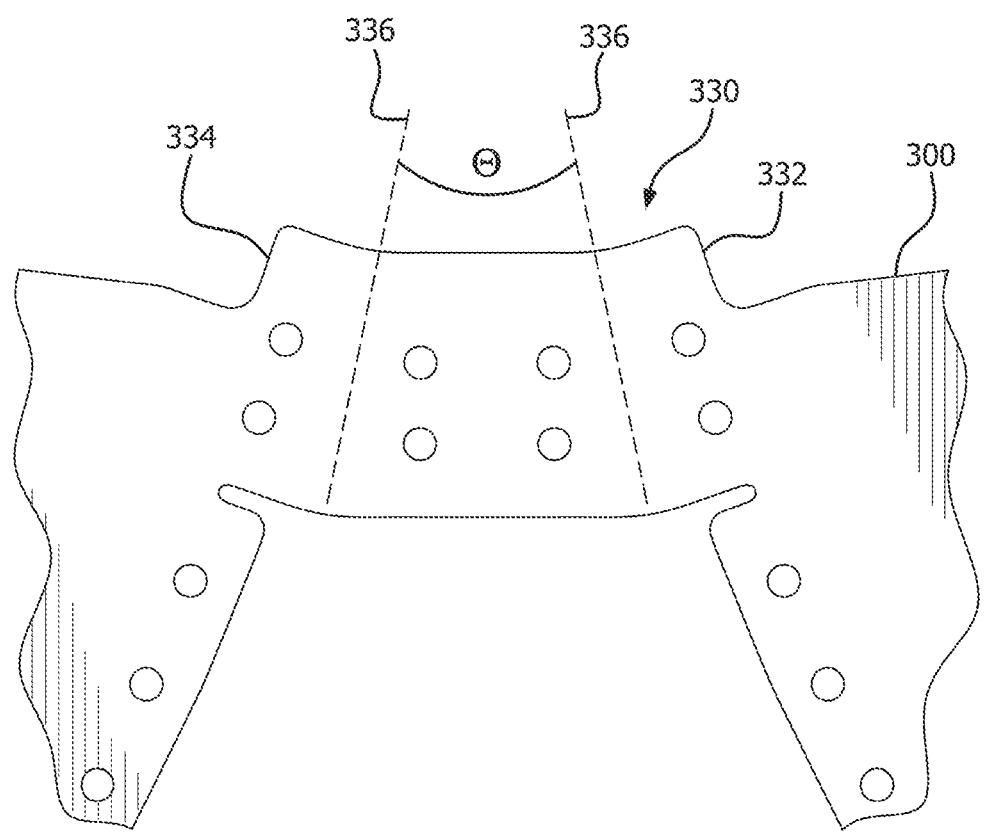
FIG. 8 is a side view of the bridge region showing fold line at an angle alpha, in accordance with another embodiment.

In accordance with an embodiment, the retention element 400 defines a relatively flat generally rectangular shape so as to have a low profile on the post outer side 212 of the commissure post 210. Due to the curvature of the annular leaflet frame 200, the sides of the retention element 400 are formed at an angle corresponding to the two loop fold lines 336 that form an angle alpha, as shown in FIG. 8, in accordance with an embodiment.

In accordance with embodiments, the retention element 400 can be flat, relatively flat, or concave on the inside (toward the center of the valve) to correspond with the radially outer convexity of commissure post 210 that the retention element 400 will be adjacent to. Each retention element 400 has a plurality of retention element apertures 408 that align with commissure post apertures 209 wherein the retention element 400 is placed against the post outer side 212 of the commissure post 210 with a portion of the bridge region 330 therebetween. A securement structure, such as, but not limited to suture 700, may be used to couple the retention element 400 to the commissure post 210. Suture may be of any suitable material, such as PTFE, PET, and nylon, among others. Stitching comprising suture 700 may be passed through these aligned commissure post apertures 209 and retention element apertures 408 and the bridge region 330 to hold each retention element 400 and the bridge region 330 to the commissure post 210. Some or all of this suture 700 may pass through the fold-over portion 324 of the leaflet 310. In that event, this suture 700 will contribute to securing the leaflet belly portion 322 of the leaflets 310 to the leaflet frame 200.

Examples of suitable materials for the retention elements 400 include various biocompatible alloys such as titanium, Elgiloy, MP35N, stainless steel, nitinol, etc., and various biocompatible engineering plastics such as acetyl polymers, PTFE, and PEEK.

Leaflet Frame Assembly

A leaflet frame assembly 234 is the assembly of the leaflet frame 200, leaflet construct 300, and the retention elements 400. The leaflet construct 300 is that portion of the valve 100 that comprises the leaflets 310 and the structure for coupling the leaflets 310 to the leaflet frame 200. In accordance with an embodiment, the leaflet construct 300 defines a contiguous cylinder defining a plurality of leaflets 310 and a bridge region 330 between each of the leaflets 310. Each bridge region defines a bridge first end 332 adjacent a first leaflet 310 and a bridge second end 334 adjacent a second leaflet 310. The leaflets extend radially inward from the leaflet frame 200 when coupled to the leaflet frame 200. Each of the leaflets 310 defines a fold-over portion 324 that is folded over and lies against a leaflet frame outer side 204 of the leaflet frame 200 and coupled thereto, such as with securement structure, such as, but not limited to suture, adhesive, thermal bonding, or other means. Each of the bridge regions 330 defines a bridge loop 338 with a coaptation neck 340 between the bridge loop 338 and the adjacent leaflets 310. The coaptation neck 340 is operable to pass through one of the post slots 217 so that the bridge loop 338 is adjacent to the outer portion of the leaflet frame 200 and the leaflets 310 extend radially inward from the leaflet frame 200. A retention element 400 is disposed within the bridge loop 338 effectively preventing the bridge loop 338 from passing through the post slot 217. The retention element 400 may be coupled to the commissure post 210, such as with suture, adhesive, thermal bonding, or other means. The fold-over portion 324 of each of the leaflets 310 is folded around an inflow edge of the leaflet frame 200 and coupled thereto, such as with suture, adhesive, thermal bonding, or other means.

In accordance with an embodiment, each bridge region 330 is wrapped around a retention element outer side 412 to the retention element inner side 414 of one of the retention elements 400 with the bridge first end 332 wrapped across the retention element inner side 414 to adjacent a dividing line 416 that vertically bisects the retention element 400, from a first direction and the bridge second end 334 wrapped across the retention element inner side 414 to adjacent the dividing line 416 from an opposite direction, wherein the bridge first end 332 and bridge second end 334 are adjacent to each other to define a coaptation neck 340.

In accordance with an embodiment, the leaflet frame assembly 234 is provided with means for coupling to a native tissue annulus, and thus the leaflet frame assembly 234 is a prosthetic heart valve 100. In an embodiment, a sewing cuff 600 is coupled to the leaflet frame assembly 234, where the sewing cuff is operable to be sutured to the native tissue annulus. In another embodiment, a base frame 500 comprising a sewing cuff 600 is coupled to the leaflet frame assembly 234.

One possible way to characterize the benefits of some embodiments presented herein is the effect of the bridge region 330 being a continuous member, that is, no seams or breaks. Any force tending to pull or extract the bridge region 330 through the post slot 217 is countered by the tensile strength of the material that the bridge region 330 comprises. The forces on the leaflets 310 during use are greatest at the commissure posts 210 tending to pull the leaflets 310 away from the commissure posts 210. The coupling of the leaflet construct 300 to the leaflet frame 200 at the commissure posts 210, in accordance with these embodiments, does not rely solely on the suture 700 but also the retention element 400 that prevents the bridge region 330 from passing through the post slot 217. It is understood that sutures, in general, tend to loosen and fail over a period of time, especially in regions of high stress. In these embodiments, the suture 700 that couples the bridge region 330 to the commissure post 210 may loosen or fail but the retention element 400 continues to prevent the bridge region 330 from passing through the post slot 217 preventing failure of the valve 100.

Further, the retention element 400 provides a clamping force between a portion of the bridge region 330 and the post outer side 212 of the commissure post 210 during operation of the valve 100. This clamping force is the result of the retention element 400 being larger than the post slot 217 which prevents the bridge region 330 from passing through the post slot 217. The clamping force does not rely on the strength of the suture 700 or the tension of the suture on the bridge region 330 and the commissure posts 210.

This clamping force may tend to distribute the forces on the bridging region 330 reducing peak stresses that might be applied at the suture 700 and apertures 999. Further the clamping force is the primary mode of transferring the forces from the leaflets 310 to the leaflet frame 200 rather than merely relying on the stitching of the leaflets 310 to the leaflet frame 200. Further, the angle alpha of the two loop fold lines 336 allows for a substantially equal distribution of stresses over the coaptation neck 340 between the bridge loop 338 and the adjacent leaflets 310 whereby reducing the peak stresses in the coaptation neck 340.

In accordance with these embodiments, the leaflets 310 extend perpendicular from the leaflet frame 200, as shown in FIG. 5. The leaflets 310 extend from the post slot 217 in a direction perpendicular to the post inner side 214 As such, the leaflets 310 exhibit a bias toward the closed position. This is beneficial in that the valve 100 will tend to close earlier during the phase of the cardiac cycle where the blood is decelerating or reversing. An earlier closure will tend to reduce back flow through the valve 100.

The design and manufacturing process (including the various components and the way of assembling those components) greatly reduce possible stress concentration at the leaflet frame-leaflet junction by distributing the load more evenly. These design and manufacturing process aspects also (1) reduce the burden of extensive and demanding suturing, (2) increase the consistency of valve manufacturing results, and (3) increase the service life of a resulting valve as a consequence of all of the foregoing factors.

Instead of or in addition to suture, chemical bonds and/or adhesives can be used between the leaflet frame 200 and the fold-over portion 324 of the leaflet construct.

The bridge regions 330 are passed through the post slot 217 in a number of ways. In accordance with an embodiment, the bridge region 330 is formed into a narrow bridge loop 338 which is passed through the post slot 217 from the leaflet frame inner side 202 to the leaflet frame outer side 204. A retention element 400 may then be inserted into the bridge loop 338 preventing the bridge loop 338 from being passed back through the post slot 217.

Figure 7:
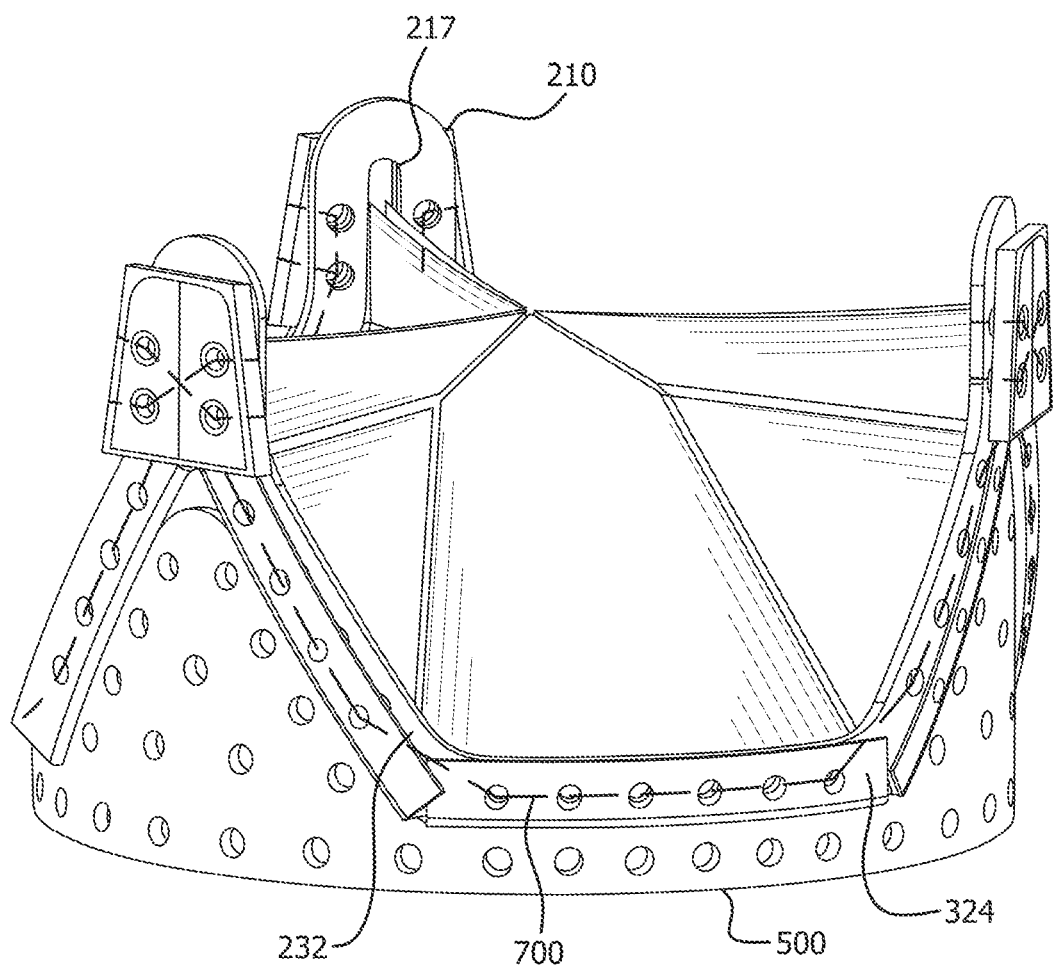
FIG. 7 is a perspective view of a leaflet frame assembly and a base frame, in accordance with the embodiment of the valve of FIG. 1A.

In accordance with embodiments, the leaflet frame 200, leaflet construct 300 and the retention elements 400 have matching and radially aligned apertures for receiving suture. The fold-over portion 324 and the bridge regions 330 containing a retention element 400 are coupled to the leaflet frame by suturing through these matching apertures. The dashed lines in FIG. 7 show an illustrative suture pattern.

Base Frame

The base frame 500 is a generally annular member defining a base frame lumen 550 having a base frame inner side 502 and a base frame outer side 504, as shown in FIGS. 3 and 4. The base frame 500 may provide structural, load-bearing support to the leaflet frame 200. In addition, the base frame 500 can be configured to provide positive engagement to the recipient tissue at the implantation site.

In accordance with an embodiment, the base frame 500 defines a plurality of triangular regions 526 extending away from the base frame inflow edge 520. The leaflet frame 200 may comprise corresponding triangular openings 256 defined by two leaflet window sides 223 of adjacent leaflet windows 222 of the leaflet frame 200 define two sides of an isosceles triangle on the leaflet frame inflow edge 220. The triangular openings 256 are operable to receive the triangular regions 526 of the base frame 500 therein.

The base frame 500 can comprise any metallic or polymeric material that is generally biocompatible. For example, the base frame 500 can comprise a material, such as, but not limited to nitinol, cobalt-nickel alloy, stainless steel, and polypropylene, acetyl homopolymer, acetyl copolymer, ePTFE, other alloys or polymers, or any other biocompatible material having adequate physical and mechanical properties to function as described herein.

The base frame 500 can be etched, cut, laser cut, or stamped into a tube or a sheet of material, with the sheet then formed into an annular structure.

In accordance with embodiments, the base frame 500 can be configured to provide positive engagement to an implant site. In an embodiment, the valve 100 further includes a sewing cuff 600 coupled about the base frame 500, as shown in FIGS. 1A and 1B, that is operable to accept suture so as to be sewn to a tissue orifice. It is understood that conventional, surgical techniques to implant prosthetic valves can be used to implant the valve 100, in accordance with embodiments.

It is appreciated that other elements or means for coupling the valve 100 to an implant site are anticipated. By way of example, but not limited thereto, other means, such as mechanical and adhesive means may be used to couple the valve 100 to a synthetic or biological conduit.

In another embodiment, the valve 100 further comprises a base frame 500, as shown in FIGS. 3 and 4. The base frame 500 is coupled to a leaflet frame inflow edge 220 of the leaflet frame 200. The base frame 500 is provided with base frame apertures 508 that may be used to suture the base frame 500 to the leaflet frame 200 using suture 700. An advantage of a separate leaflet frame 200 and base frame 500 is that they may have different physical characteristics. By way of example, a relatively less stiff leaflet frame 200 supporting the leaflets 310 can be more likely to reduce the loading encountered by the opening and closing leaflets 310 as compared to a stiffer leaflet frame 200. The leaflet frame 200 having a relatively less stiff property may reduce leaflet accelerations and reduce the closing stresses on the leaflets 310. Wherein the base frame 500 may be more stiff which would be more suitable for suturing to the native tissue orifice. The base frame 500 may resist the compressive forces that may be encountered at the implant site, for example.

In embodiments of the valve 100, the inclusion of a base frame 500 and a leaflet frame 200 provides a means for providing different physical properties for each of the base frame 500 and the leaflet frame 200 suitable for a particular purpose. In accordance with an embodiment, the base frame 500 is stiffer as compared with the leaflet frame 200. The base frame 500, when engaged to the implant site, such as, but not limited to a tissue orifice, is rigid enough to not significantly deform under physiological loading.

The physical properties of the base frame 500 and the leaflet frame 200 depends, in part, on the size, shape, thickness, and material property of the base frame 500 and the leaflet frame 200.

Stiff and stiffness, as used herein and as is commonly used in engineering, is a measure of the resistance to deformation given by a base. Stiff and stiffness is a function of, among other things, material properties, the shape of the object, and the boundary conditions on the object. Stiffness of the leaflet frame 200 (see FIG. 1A) may be measured by any number of methods known in the art.

Sewing Cuff

The valve 100 may be provided with a sewing cuff 600 adjacent the base frame 500, as shown in FIGS. 1A and 1B. The sewing cuff 600 is operable to provide structure that receives suture for coupling to the implant site. The sewing cuff 600 may comprise any suitable material, such as, but not limited to, double velour polyester and silicone. The sewing cuff 600 may be located circumferentially around the base frame 500 or perivalvular depending from the base frame 500. The sewing cuff 600 may comprise a filler material, such as, but not limited to, a silicone ring and/or PTFE felt.

Methods

The embodiments can be made utilizing methods known to one skill in the art. For example, in accordance with an embodiment, a leaflet can be made by obtaining a tube comprising one or more layers of expanded PTFE composite. Cutting a leaflet construct including a plurality of leaflets each being separated by a bridge region from the tube. Providing fold-over apertures in fold-over portions of the leaflets and bridge apertures in the bridge region. Obtaining a plurality of retention elements, each retention element defining retention element apertures. Folding each of the bridge regions into a bridge loop and defining a coaptation neck between each bridge loop and two adjacent leaflets, the bridge loops extending radially away from the tube axis. Disposing a retention element into each of the bridge loops. Suturing each retention element to the respective bridge loop passing suture through the bridge apertures and the retention element apertures that are aligned therewith. Cutting a leaflet frame from a metal tube defining leaflet frame windows and commissure posts therebetween where each commissure post defines a post slot dimensioned to receive at least a double thickness of the bridge region. Providing leaflet window frame apertures in the leaflet window frame and post apertures in the commissure posts. Disposing each coaptation neck in a respective post slot with the retention elements adjacent the post outer side and disposing the leaflets in the leaflet frame. Aligning the retention element apertures with the post apertures. Suturing each retention element to the respective commissure post passing suture through the retention element apertures and the post apertures that are aligned therewith. Folding the fold-over portions of each leaflet along the leaflet frame inflow edge and against the leaflet frame outer side aligning the fold-over apertures with the leaflet window frame apertures. And suturing each fold-over portion to the respective leaflet window frame passing suture through the fold-over apertures and the leaflet window frame apertures that are aligned therewith.

In accordance with an embodiment the method may further comprise providing strips of fabric, wrapping and sewing the fabric on the leaflet frame to provide a cushion between the leaflet frame and the leaflet construct, and trimming the fabric to approximately 3 mm from the leaflet frame outflow edge of the leaflet frame.

In accordance with an embodiment the method may further comprise cutting a base frame from a metal tube defining base frame apertures, and coupling the base frame to the leaflet frame inflow edge of the leaflet frame.

In accordance with an embodiment the method may further comprise providing a fabric tube and inserting the fabric tube through the base frame along its flow axis. Folding the fabric outflow edge of the fabric over the base frame outflow edge of the base frame. Sewing the fabric into place using suture through the base frame apertures in the base frame. Inverting the fabric inflow edge of the fabric tube over the base frame. Sewing the fabric tube into place using suture through base frame apertures along the inflow edge of the base frame. Disposing a sewing cuff insert inside a pocket defined by the inverted fabric tube and tucking the fabric tube in between the base frame and the sewing cuff insert such that all the slack of the fabric tube is removed around the sewing cuff. Placing the leaflet frame coaxially with and adjacent to the base frame and inside the fabric tube. Trimming the fabric tube approximately 5 mm from the leaflet frame outflow edge and suturing the leaflet frame to the base frame at the leaflet window base using suture passing through the respective leaflet window frame apertures and the base frame apertures. Folding the trimmed edge of the fabric tube over the leaflet frame outflow edge, tucking the trimmed edge underneath itself to conceal any frayed edges, and sewing the fabric tube to the fabric on the leaflet frame.

Example

By way of example, one embodiment of a valve was made as follows:

A surgical prosthetic heart valve was constructed in the following manner. A leaflet construct 300, including fold-over apertures 308 and bridge apertures 309, was cut from the leaflet coupon using a $CO_2$ laser according to the pattern shown in FIG. 3.

Three retention elements 400 made from PEEK, shown in FIG. 3, were sewn onto the bridge loop 338 of the bridge region 330 of the leaflet construct 300, as shown in FIGS. 5 and 6. The retention element 400 is provided with retention element apertures 408 that align with bridge apertures 309 on the leaflet construct 300. A partial view of the resulting assembly is shown in FIG. 2.

A leaflet frame 200 and base frame 500 were laser cut, including leaflet frame apertures 208 and base frame apertures 508, respectively, and electropolished from a tube of cobalt chromium (MP35N) with a 25 mm OD and 0.4 mm wall thickness, as shown in FIG. 3. The frames were cleaned in an ultrasonic bath of ethanol to remove contaminants. Three strips of polyester knit fabric were wrapped and sewn on the leaflet frame, to provide a cushion between the leaflet frame 200 and the leaflet construct 300. A post slot 217 of the commissure post 210 large enough (approximately 0.254 mm) to accommodate a double thickness of the leaflet construct 300 at the bridge region 330 was provided. The remaining polyester knit fabric was trimmed off approximately 3 mm from the leaflet frame outflow edge 224 of the leaflet frame 200 shown in FIG. 4. The leaflet construct 300 with retention elements 400 was placed onto the leaflet frame 200 by sliding each coaptation neck 340 in the post slot 217 with the retention elements 400 on the post outer side 212, as shown in FIG. 2. The retention element apertures 408 were aligned with leaflet frame apertures 208 on the leaflet frame 200 and were sewn into place with suture 700, as shown in FIG. 6. The leaflet construct 300 includes fold-over portions 324 and fold-over apertures 308 along attachment edges. The fold-over portions 324 were folded along the leaflet frame inflow edge 220 of the leaflet frame 200 up against the leaflet frame outer side 204 where fold-over apertures 308 in the fold-over portions 324 coincide with leaflet frame apertures 208 of the leaflet frame 200 and were sewn into place with suture 700 as shown in FIG. 7.

A tube of polyester knit fabric about 24 mm in diameter and at least 10 cm in length was inserted through the base frame 500 along its flow axis. The fabric outflow edge of the polyester knit fabric was folded over the base frame outflow edge 524 of the base frame 500 and sewn into place using suture 700 through base frame apertures 508 in the base frame 500 (not shown). The fabric inflow edge of the polyester knit fabric tube was inverted over the base frame 500 and sewn into place using suture 700 through base frame apertures 508 along the base frame inflow edge 520 of the base frame 500. A silicone sewing cuff insert was placed over the base frame 500 and inside of the inverted polyester knit fabric tube. The polyester knit fabric tube was tucked in between the base frame 500 and the sewing cuff insert such that all the slack was removed around the sewing cuff 600.

The leaflet frame assembly 234 comprising the leaflet frame 200, the leaflet construct 300 and retention elements 400 was coaxially placed adjacent the base frame and inside the polyester knit fabric tube. The polyester knit fabric tube was trimmed approximately 5 mm off the leaflet frame outflow edge 224. The leaflet frame 200 was sutured to the base frame 500 at the leaflet window base 225, with three sutures 700 at each of the three leaflet window bases 225 of the leaflet frame 200. The trimmed edge of the polyester knit fabric was folded over the leaflet frame outflow edge 224. The trimmed edge was tucked underneath itself to conceal any frayed edges and sewn to the polyester knit fabric on the leaflet frame.

Other Examples

Figure 9:
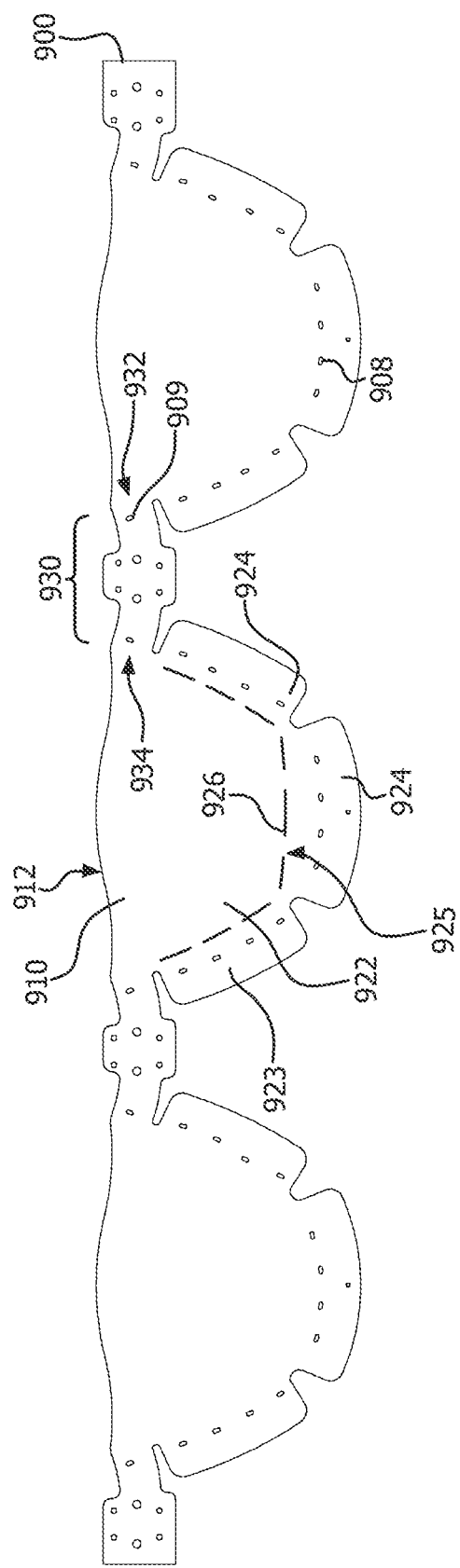
FIG. 9 is view of a leaflet construct unrolled to a flat orientation, according to some embodiments.

FIG. 9 is similar to FIG. 3 and shows a top view of another example of a leaflet construct that has been longitudinally cut and laid open. As shown, a leaflet construct 900 includes a plurality of leaflets 910. The leaflet construct 900 may be cut from a sheet of polymer material that has been cut into a shape like that shown in FIG. 3 and subsequently coupled together into an annular shape, as similarly discussed above with regard to leaflet construct 300. Alternatively, the leaflet construct 900 may be formed by way of one or more compression or injection molding processes, as discussed above. It will be appreciated that the operation of leaflet construct 900 and securing of the leaflet construct 900 to a corresponding leaflet frame is similar to that discussed above with regard to leaflet construct 300. However, it will also be appreciated that leaflet construct 900 is different in appearance from leaflet construct 300.

As shown, each of the leaflets 910 has a leaflet belly portion 922, and a fold-over portion 924. The leaflet belly portion 922 of each leaflet 910 is the operating portion of the leaflet 910 when in a finished and implanted valve 100. The fold-over portion 924 of each leaflet 910 is the portion that is used to secure the leaflet 910 to the leaflet frame 200. In some examples a fold 926 (which is similar to fold 326, discussed above) may be formed between the leaflet belly portion 922 and the fold-over portion 924 of a respective one of the leaflet sides 923 and leaflet base 925, respectively, of the leaflets 910, such that one or more portions of a corresponding leaflet frame, such as leaflet frame 200, may be received therein.

In accordance with some examples, each leaflet 910, at the folds 926, has substantially the shape of an isosceles trapezoid. In some examples, the two leaflet sides 923 diverge from the leaflet base 925.

In accordance with other embodiments of the valve 100, each leaflet 910 includes a central region 929 and two side regions 928 on opposite sides of the central region 929. In some examples, the central region is defined upon securing the leaflet 910 to a leaflet frame. The central region 929 is generally defined by a shape substantially that of an isosceles trapezoid defined by the two side regions 928, the leaflet base 925 and the leaflet free edge 912. When secured to the leaflet frame, each of the side regions 928 has a shape substantially that of a triangle and each are defined by the central region 929, one of the leaflet sides 923, and the leaflet free edge 912.

In some examples, as similarly discussed above, the leaflet belly portion 922 of each leaflet 910 includes enough material between corresponding commissure posts of a leaflet frame so that the leaflet free edges 912 of the three leaflet belly portions 922 can come together or coapt in the interior of the valve 100 to close the valve 100 as discussed herein.

Similarly, in some examples, a bridge region 930 is situated between each of the leaflets 910. In some examples, the bridge region 930 is operable to be formed into a bridge loop 938 having a generally rectangular shape, folding about two loop fold lines 936 as similarly discussed above with regard to leaflet construct 300. In some examples, leaflet construct is thus operable to interface with retention element 400 in the same manner as leaflet construct 300. However, as discussed in greater detail below, leaflet constructs 900 and 300 may also interface with an outer frame, such as outer frame 100, in lieu of retention element 400.

In accordance with some embodiments, the leaflet construct 900 includes a biocompatible material that is not of a biological source and that is sufficiently compliant and strong for the particular purpose, such as a biocompatible polymer. In an embodiment, the leaflet construct 900 comprises a membrane that is combined with an elastomer or elastomeric material to form a composite material, as discussed above. In accordance with other embodiments, the biocompatible material that makes up the leaflet construct 900 comprises a biological material, such as, but not limited to, bovine pericardium.

The shape of the leaflets 910 are defined in part by a shape of a leaflet frame to which the leaflets 910 are secured and the leaflet free edge 912. The shape of the leaflets 910 can also be defined by the structures and processes used to manufacture the valve 100, as discussed above with regard to leaflet construct 300. In accordance with some embodiments, the shape of the leaflets 910 also depends in part on molding the leaflets 910 using molding and trimming processes to impart a predetermined shape to the leaflets 910. Operation of the leaflet construct 900 is similar to that of leaflet construct 300, discussed above.

While the embodiments and examples discussed above include securing leaflet constructs, such as leaflet constructs 300 and 900 to leaflet frames by way of one or more retention elements that are individually disposable within the bridge loop formed by the bridge region of the leaflet construct, to effectively prevent the bridge loop from passing through the post slot of the leaflet frame, it will be appreciated that the bridge loop formed by the bridge region of the leaflet construct may be secured to an outer frame that surrounds the leaflet frame. As will be discussed in greater detail below, such configurations provide the above discussed advantages of equally distributing stresses over the coaptation neck between the bridge loop and the adjacent leaflets, and reducing the peak stresses in the coaptation neck. Such configurations also provide that the fold-over portion (e.g., 324 and 924) that is generally folded over and lies against an outer side of a leaflet frame can be sandwiched or otherwise situated between the leaflet frame and the outer frame. Such a configuration generally provides for a desirable stress distribution in comparison with nonfolded designs. In particular, it has been observed that such a configuration provides for a more desirable stress distribution along the attachments surface in comparison with known suturing methods where stress is localized at the apertures in the leaflet through which the sutures pass.

In various examples, the various leaflet constructs discussed herein may include one or more portions, regions, section, zones or areas that are configured to support and promote tissue ingrowth. In some examples, an underlying structure of the leaflet construct is configured to support tissue ingrowth. In some other examples, one or more tissue ingrowth curtains may additionally or alternatively be applied to one or more portions of the leaflet construct. That is, in some examples, a construct (such as a membrane or film or coating) may be applied to the leaflet construct that is configured to support and encourage the ingrowth and proliferation of tissue.

Turning now to FIGS. 10A to 10E, a prosthetic valve 100 is illustrated and includes a leaflet frame 200, an outer frame 800, and a leaflet construct 900. FIG. 10A is an outflow side perspective view of a prosthetic heart valve 100. FIG. 10B is a side view of the prosthetic heart valve 100 including a fabric 1000 covering the leaflet frame 200 and the outer frame 800 and a suture cuff 600. FIG. 10C is a top view of the outflow side of the prosthetic heart valve 100 with the fabric 1000 covering the leaflet frame 200 and the outer frame 800 and the suture cuff 600. FIG. 10D is cross section view of the prosthetic heart valve 100 of FIG. 10B taken along line 10D-10D. FIG. 10E is cross section view of the prosthetic heart valve 100 of FIG. 10C taken along line 10E-10E.

The outer frame 800 is configured to interface with the leaflet construct (e.g., 300 or 900) and the leaflet frame 200, and is operable to hold and support the leaflet construct during operation of the prosthetic valve 100. The outer frame 800 is an annular structural element and is configured such that the leaflet frame 200 can be disposed within an interior region defined by the outer frame 800 such that the leaflet frame 200 and the outer frame 800 are coaxially aligned. In various examples, the outer frame 800 includes a plurality of commissure posts that are configured to interface with the leaflet construct of the prosthetic valve and secure the leaflet construct to the outer frame 800. For example, as shown the outer frame 800 includes a plurality of commissure posts 810. The commissure posts 810 extend from a base 806 generally along a central axis of the outer frame 800 to an outer frame commissure tip 819. The commissure posts 810 are spaced from one another in a manner that corresponds with the commissure posts 210 of the leaflet frame 200. For instance, in some examples, the commissure posts 810 extend from the base 806 such that the commissure posts 810 extend substantially parallel with the commissure posts 210 of the leaflet frame 200.

In some examples, the outer frame 800 is comprised of a plurality of individual keystones that are assembled together to form the outer frame 800. That is, in some example, the outer frame 800 is not a single monolithic structure. For instance, in some examples, two or more individual keystones are assembled together to form the outer frame 800. In some examples, each keystone includes a commissure post, such as commissure post 810. In some examples, the plurality of keystones are assembled together such that they form the outer frame 800. In some examples, the keystones are assembled together via one or more sutures. Together, the plurality of assembly keystones define a contiguous annular structural element that is the outer frame 800. In some examples, a ring element, such as a coil or a solid ring, is additionally or alternatively disposed about a periphery of the assembled keystones. For example, as shown in FIGS. 10A and 10E a ring element 850 is disposed about the outer frame 800. In some examples, such a ring element helps provide radial stiffness or hoop strength to the outer frame 800.

Alternatively, in some examples, the outer frame 800 is formed as a single monolithic unit. In some examples, the outer frame 800 may be cut from a sheet of material that then appropriately shaped such that its ends are coupled into an annular shape, as similarly discussed above with regard to leaflet construct 300. Those of skill will thus appreciate that the outer frame 800 can be etched, cut, laser cut, stamped, three-dimensional printed, molded, among other suitable processes, into an annular structure or a sheet of material, with the sheet then formed into an annular structure. Alternatively, the leaflet construct 900 may be formed by way of one or more compression or injection molding processes, as discussed above. Regardless of the form by which the outer frame 800 is constructed, the commissure posts 810 are generally equally spaced from one another around the outer frame 800.

The outer frame 800 can comprise, such as, but not limited to, any elastically deformable metallic or polymeric material that is generally biocompatible. The outer frame 800 can comprise a shape-memory material, such as nitinol, a nickel-titanium alloy. Other materials suitable for the outer frame 800 include, but not limited to, other biocompatible materials such as other titanium alloys, stainless steel, cobalt-nickel alloy, Elgiloy, MP35N, as well as various biocompatible plastics such as acetyl polymers, PTFE, PET, PEEK, polypropylene, acetyl homopolymer, acetyl copolymer, other alloys or polymers, rapid plastics (SLA) or sintered metals, or any other material that is generally biocompatible having adequate physical and mechanical properties to function as and outer frame 800 as described herein.

As shown in FIGS. 10A to 10E, the outer frame 800 generally includes a frame inner side 802 and a frame outer side 804 opposite the frame inner side 802. Similarly, each commissure post 810 has a post outer side 812 and a post inner side 814 opposite the post outer side 812. In various examples, the post inner and outer sides 812 and 814 correspond with the outer frame inner and outer sides 802 and 804, respectively.

The prosthetic valve 100 shown in FIGS. 10A to 10E is configured such that the outer frame 800 is situated coaxial with the leaflet frame 200. In some examples, as shown, the outer frame 800 is situated adjacent the leaflet frame 200 such that the base 806 of the outer frame 800 is adjacent one or more of the inflow edge 220, the outflow edge 224 and the window base 225 of the leaflet frame 200. Thus, in some examples, the portion of the leaflet frame outer side 204 between the inflow and outflow edges 220 and 224 of the leaflet frame 200 is situated adjacent to and radially inwardly of the frame inner side 802 of the base 806 of the outer frame 800, as shown in FIG. 10E. Thus, in such a configuration, unlike the arrangement including the base frame 500 illustrated and described in association with FIG. 7, the outer frame 800 does not form part of an interior region of the prosthetic valve. Instead, as shown in FIGS. 10A to 10E, the frame inner side 802 of the base 806 of the outer frame 800 is positioned radially outwardly of the leaflet frame outer side 204, as shown in FIG. 10E. As shown, the fold-over portion 924 of the leaflet 910 is situated between the leaflet frame 200 and the outer frame 800. Specifically, as shown the fold-over portion 924 of the leaflet 910 is situated between the frame outer side 204 of the leaflet frame 200 and the frame inner side 802 of the outer frame 800. Additionally, as shown, such a configuration provides that a portion of the leaflet 910 is exposed on the inflow side of the prosthetic valve 100.

Similar to the retention element 400 discussed above, the commissure post 810 of the outer frame 800 operates to secure the leaflet construct to the outer frame 800 to form the prosthetic valve 100. In various examples, the leaflet construct is secured to the outer frame 800 prior to the leaflet frame 200 being secured to the outer frame 800, and/or prior to the leaflet construct (e.g., 900 or 300) being secured to the leaflet frame 200. In some such examples, the commissure posts 810 are disposed within the bridge loop (e.g., 938 or 338) of the leaflet construct (e.g., 900 or 300) prior to securing the leaflet construct to the outer frame 800 and/or prior to securing the leaflet construct to the leaflet frame 200. Specifically, the commissure posts 810 of the outer frame 800 are operable to be disposed within the bridge loop (e.g., 938 or 338) formed by the bridge region 330 of the leaflet construct, thereby effectively preventing the bridge loop (e.g., 938 or 338) from passing through the post slot of 217 of the leaflet frame 200, as discussed above. In various examples, each commissure post 810 has a width that is larger than a width of the post slot 217 of the leaflet frame 200. Moreover, as similarly discussed above, the size of the bridge loop (e.g., 938 or 338) should correspond to the size of the portion of the commissure post 810 about which it is disposed to prevent excess material of the bridge region 330 from being pulled through the post slot 217, thereby changing a geometry of a corresponding leaflet.

The commissure post 810 generally defines a relatively flat, rectangular cross section so as to have a low profile on the post outer side 212 of the commissure post 210 of the leaflet frame 200. In some example, the commissure post 810 additionally includes a projection that is configured to extend between opposing coapting necks extending through a post slot 217 of the leaflet frame 200. For example, as shown in FIG. 10D, the commissure post 810 of the outer frame 800 includes a projection 816 extending between leaflets 910 of the coaptation neck 940 passing through the post slot 217 of the leaflet frame 200. In some examples, the projection may extend entirely through the post slot 217. For example, the projection 816 may be configured such that the projection 816 extends away from the post inner side 814 by an amount sufficient for the projection 816 to extend radially inwardly of the leaflet frame inner side 202 (e.g., post inner side 214) when the leaflet frame 200 is coupled with the outer frame 800. In some other examples, the projection may extend only partially into the post slot 217. For example, the projection 816 may be configured such that the projection 816 extends away from the post inner side 814 by an amount sufficient for the projection 816 to extend radially inwardly of the leaflet frame outer side 204 (post outer side 212) yet terminate radially outwardly of the leaflet frame inner side 202 (post inner side 214) when the leaflet frame 200 is coupled with the outer frame 800. It will be appreciated that in some other examples, the projection 816 may be configured to terminate at the leaflet frame inner side 204, or the leaflet frame outer side 202, or radially outwardly of the leaflet frame outer side 202.

In some examples, such a projection provides that a gap can be formed between adjacently situated leaflets at the commissure post 210. In some examples, the formation of such a gap can help minimize the potential for undesirable stasis at or proximate the commissure post 210. Accordingly, it will be appreciated that a width of the projection forming the gap can be increased or decreased to achieve a desired gap between coapting leaflets adjacent the commissure post 210. It will be appreciated that a width of the post slot 217 in the commissure post 210 of the leaflet frame 200 will generally correspond to the width of the projection 816, such that the post slot 217 is configured to accommodate the projection 816 and the plurality of leaflets (e.g., 910 or 310) extending therethrough. However, it will also be appreciated that, in some examples, it may undesirable to form a gap between coapting leaflets at the commissure post 210. In such instances, the commissure post 810 of the outer frame 800 may be configured without the incorporation of the projection 816.

In accordance with embodiments, the commissure post 810 can be flat, relatively flat, or concave on the inside (toward the center of the prosthetic valve 100) to correspond with the radially outer convexity of commissure post 210 that the commissure post 810 will be adjacent to. In various example, similar to the retention elements 400, the commissure posts 810 may include one or more apertures that align with commissure post apertures 209 wherein the commissure post 810 is placed adjacent the post outer side 212 of the commissure post 210. Similarly, in some examples, a securement structure, such as, but not limited to suture 700, may be used to couple the commissure post 810 to the commissure post 210. For example, as discussed above, stitching comprising suture 700 may be passed through aligned commissure post apertures 209 and apertures of the commissure post 810, as well as through the bridge region of the leaflet construct to couple together each of the commissure post 810, the leaflet construct, and the commissure post 210.

Each of the leaflet frame 200, the outer frame 800, and the suture cuff 600 may be individually wrapped or covered with the fabric 1000 prior to being coupled one another. Alternatively, in some examples, the fabric 1000 may be coupled to or otherwise disposed about one or more of the leaflet frame 200, the outer frame 800, and the suture cuff 600 after one or more of the leaflet frame 200, the outer frame 800, and the suture cuff 600 have been coupled together. For example, the outer frame 800 and the suture cuff 600 may be coupled together and then covered with the fabric 1000, after which the leaflet frame 200 is coupled with the outer frame 800. Additionally, in various examples, the leaflet construct may be secured to the outer frame prior to (or alternatively after) the fabric is coupled to or otherwise disposed about the outer frame 800.

Figure 11A:
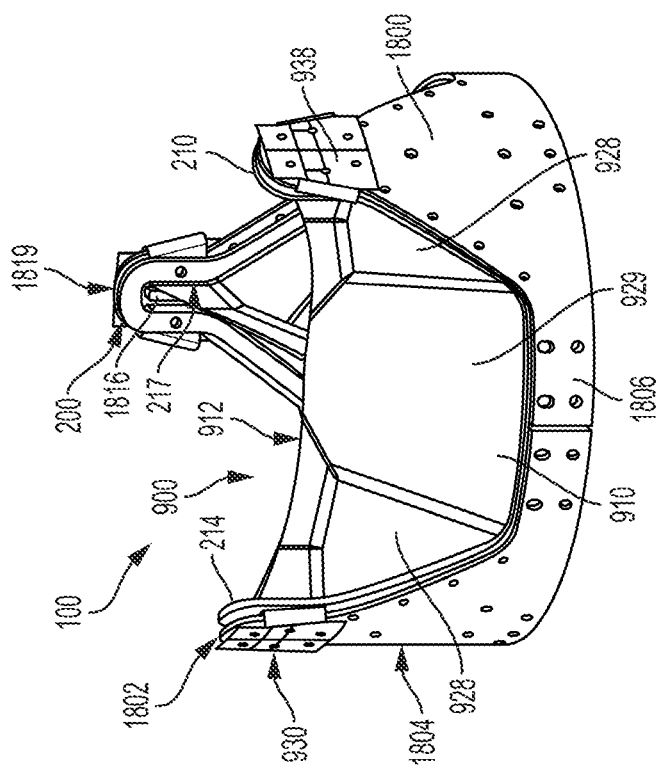
FIG. 11A is an outflow side perspective view of a prosthetic heart valve, according to some embodiments.
Figure 11B:
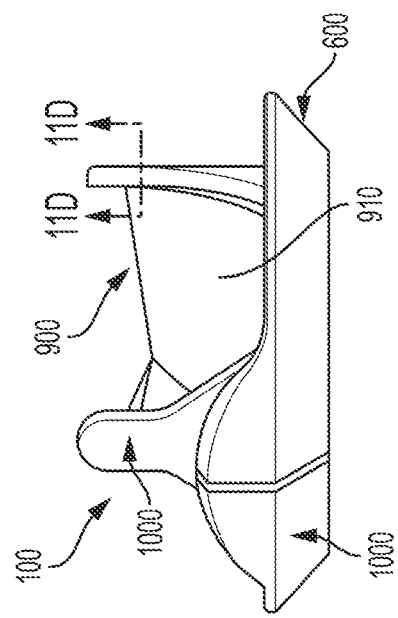
FIG. 11B is a side view of the prosthetic heart valve of FIG. 11A, according to some embodiments.
Figure 11C:
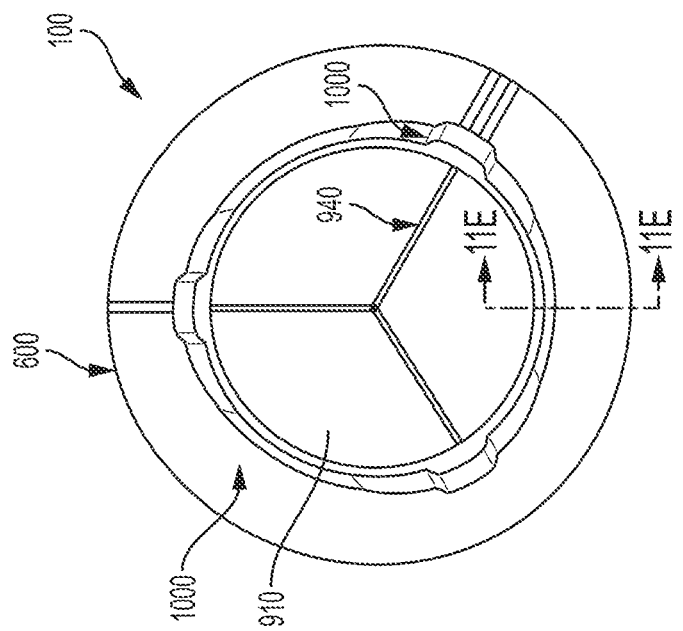
FIG. 11C is a top view of the outflow side of the prosthetic heart valve of FIG. 11A, according to some embodiments.

Turning now to FIGS. 11A to 11E, a prosthetic valve 100 is illustrated and includes a leaflet frame 200, an outer frame 1800, and a leaflet construct 900. FIG. 11A is an outflow side perspective view of a prosthetic heart valve 100. FIG. 11B is a side view of the prosthetic heart valve 100 including a fabric 1000 covering the leaflet frame 200 and the outer frame 1800 and a suture cuff 600. FIG. 11C is a top view of the outflow side of the prosthetic heart valve 100 with the fabric 1000 covering the leaflet frame 200 and the outer frame 1800 and the suture cuff 600. FIG. 11D is cross section view of the prosthetic heart valve 100 of FIG. 11B taken along line 11D-11D. FIG. 11E is cross section view of the prosthetic heart valve 100 of FIG. 11C taken along line 11E-11E.

In various examples, the outer frame 1800 includes a plurality of commissure posts that are configured to interface with the leaflet construct of the prosthetic valve and secure the leaflet construct to the outer frame 1800. For example, as shown the outer frame 1800 includes a plurality of commissure posts 1810. The commissure posts 1810 extend from a base 1806 generally along a central axis of the outer frame 1800 to an outer frame commissure tip 1819. The commissure posts 1810 are spaced from one another in a manner that corresponds with the commissure posts 210 of the leaflet frame 200. For instance, in some examples, the commissure posts 1810 extend from the base 1806 such that the commissure posts 1810 extend substantially parallel with the commissure posts 210 of the leaflet frame 200.

In some examples, the outer frame 1800 is similar to the outer frame 800, discussed above in that the outer frame 1800 may be comprised of a plurality of individual keystones that are assembled together to form the outer frame 1800, or alternatively, may be formed as a single monolithic unit, as discussed above. Similarly, the outer frame 1800 can comprise, such as, but not limited to, any elastically deformable metallic or polymeric material that is generally biocompatible, as discussed above.

As shown in FIGS. 11A to 11E, the outer frame 1800 generally includes a frame inner side 1802 and a frame outer side 1804 opposite the frame inner side 1802. Similarly, each commissure post 1810 has a post outer side 1812 and a post inner side 1814 opposite the post outer side 1812. In various examples, the post inner and outer sides 1812 and 1814 correspond with the outer frame inner and outer sides 1802 and 1804, respectively. As discussed further below, in some examples, the frame inner side 1802 includes a first surface 1802a and a second surface 1802b that is radially offset from the first surface 1802a.

The prosthetic valve 100 shown in FIGS. 11A to 11E is configured such that the outer frame 1800 is situated coaxial with the leaflet frame 200. In some examples, as shown, the outer frame 1800 is situated adjacent the leaflet frame 200 such that the base 1806 of the outer frame 1800 is adjacent one or more of the inflow edge 220, the outflow edge 224 and the window base 225 of the leaflet frame 200. Thus, in some examples, the portion of the leaflet frame outer side 204 between the inflow and outflow edges 220 and 224 of the leaflet frame 200 is situated adjacent to and radially inwardly of the frame inner side 1802 of the base 1806 of the outer frame 1800, as shown in FIG. 11E. As shown in FIGS. 11A to 11E, the frame inner side 1802 of the base 1806 of the outer frame 1800 is positioned radially outwardly of the leaflet frame outer side 204, as shown in FIG. 11E. Moreover, in some examples, the outer frame 1800 extends beyond the inflow edge 220 of the leaflet frame 200 such that an inflow edge 1824 of the outer frame 1800 defines an inflow edge of the prosthetic valve 100. That is, unlike the configuration illustrated and described above with regard to FIGS. 10A to 10E, the prosthetic valve 100 is configured such that the outer frame 1800 is positioned radially outwardly of the frame outer side 204 of the leaflet frame 200 and such that the leaflet frame 200 is positioned between the outer frame commissure tip 1819 of the outer frame 1800 and the inflow edge 1824 of the outer frame 1800.

In various examples, the outer frame 1800 is configured to interface with the leaflet construct (e.g., 300 or 900) and the leaflet frame 200, and is operable to hold and support the leaflet construct during operation of the prosthetic valve 100. The outer frame 1800 is an annular structural element and is configured such that the leaflet frame 200 can be disposed within a portion of an interior region defined by the outer frame 1800 such that the leaflet frame 200 and the outer frame 1800 are coaxially aligned. In various examples, a base 1806 of the outer frame 1800 is configured such that when the leaflet frame 200 is received with in the interior region defined by the outer frame 1800, the leaflet frame outer side 204 is situated adjacent to a first portion of the outer frame 1800 and the inflow edge 220 of the leaflet frame 200 is situated adjacent a second portion of the outer frame 1800.

Specifically, as shown in FIG. 11E, the outer frame 1800 includes a base portion 1806 that includes a first portion 1818 and a second portion 1820. In various examples, the first portion 1818 defines a frame outer side 1804 of the outer frame 1800, and defines a first surface 1802a of a frame inner side 1802. The second portion 1820 extends radially inwardly from the first portion 1818 and defines a second surface 1802b of the frame inner side 1802 that is radially inwardly offset relative to the first surface 1802a of the frame inner side 1802. The first and second surfaces 1802a and 1802b of the frame inner side 1802 extend generally along a longitudinal axis of the outer frame 1800.

In various examples, a shoulder surface 1822 extends between the first and second surfaces 1802a and 1802b of the frame inner side 1802. In some examples, the shoulder surface 1822 extends transverse to the longitudinal axis of the outer frame. In various examples, the shoulder surface 1822 is thus an annular surface situated between the first and second surfaces 1802a and 1802b of the frame inner side 1802. In some examples, the shoulder surface 1822 is situated opposite an inflow edge 1824 of the outer frame 1800, as shown in FIG. 11E. In various examples, the offset relationship between the first and second surfaces 1802a and 1802b of the frame inner side 1802 provides that the leaflet frame 200 can be received by the outer frame 1800 such that the outer frame 1800 includes one or more portions that are situated adjacent the leaflet frame outer side 204 and such that the outer frame 1800 includes one or more portions that are situated adjacent the inflow edge 220 of the leaflet frame 200, as shown in FIG. 11E.

In some example, the first portion and the second portion are formed as a single monolithic unit. In some other examples, the first and second portions are formed independent of one another. In some such examples, the first and second portion are coupled together to form the outer frame 1800. It will be appreciated that the first and second portions may be coupled together according to any known methods.

With continued reference to FIG. 11E, in some examples, the leaflet 910 is situated between the leaflet frame 200 and the outer frame 1800 such that the fold-over portion 924 of the leaflet 910 is situated between the leaflet frame 200 and the outer frame 1800. Specifically, as shown in FIG. 11E, the leaflet 910 is situated between the frame outer side 204 of the leaflet frame 200 and the first surface 1802a of the frame inner side 1802 of the outer frame 1800. Additionally, as shown, the leaflet 910 is situated between the inflow edge 220 of the leaflet frame 200 and the shoulder surface 1822 of the outer frame 1800. In various examples, the fold-over portion 924 of the leaflet 910 is positioned between those adjacently situated portions of the leaflet frame 200 and the outer frame 1800 mentioned above.

In various examples, a shape of the fold-over portion 924 of the leaflet is based, at least in part, on its position between the geometries of leaflet frame 200 an the outer frame 1800. For example, as the leaflet frame 200 is secured to the outer frame 1800, the leaflet frame inflow edge 220 and/or the leaflet frame outer side 204 engage the fold-over portion 924 of the leaflet 910 and cause the fold-over portion 924 of the leaflet 910 to fold around the leaflet frame inflow edge 220 and the leaflet frame outer side 204. In some examples, the leaflet construct (e.g., 300 or 900) is secured to the outer frame 1800 prior to securing the leaflet frame 200 and the outer frame 1800 together. In various examples, the leaflet construct is secured to the outer frame such that the fold-over portions 924 of the leaflets 910 is secured to the first surface 1802a of the outer frame inner side 1802. Thus, it will be appreciated that as the leaflet frame 200 is secured to the outer frame 1800, the portions of the fold-over regions 924 of the leaflets 910 that are secured to the outer frame 1800 remain secured to the outer frame 1800 such that the remaining portions of the fold-over regions 924 of the leaflets 910 are drawn into the regions between the adjacently situated surfaces and edges of the leaflet frame 200 and the outer frame 1800, as discussed above. In various examples, as these portions of the fold-over regions 924 are drawn between the leaflet frame 200 and the outer frame 1800, these portions are forced to wrap around the leaflet frame 200 from the leaflet frame inflow edge 220 to the leaflet frame outer side 204 as shown in FIG. 11E.

Put differently, in various examples, prior to securing the leaflet frame 200 with the outer frame 1800, a leaflet construct (e.g., 900 or 300) is secured to the first surface 1802a of the frame inner side 1802 of the outer frame 1800 such that the fold-over portions 924 of the leaflets adopt a first profile. In some examples, upon securing the leaflet frame 200 with the outer frame 1800, one or more of the leaflet frame inflow edge 220 and the leaflet frame outer side 204 engage the leaflet 910 (e.g., the fold-over portion 924 of the leaflet 910) and cause the leaflet 910 to adopt a second different profile.

In various examples, by securing the leaflet construct to the outer frame 1800 between the outer frame 1800 and the leaflet frame 200, as mentioned above, a surface area of the leaflet 910 interfacing with the leaflet frame 200 and the outer frame 1800 is increased relative to the configurations illustrated in FIGS. 7 and 10A to 10E.

Additionally, as discussed further below, the configuration illustrated in FIGS. 11A to 11C provides that, in examples where one or more of the outer frame 1800 and the leaflet frame 200 are covered with a material suitable for supporting tissue ingrowth, the inflow and outflow sides of the leaflet 910 are positioned adjacent the leaflet frame and the outer frame. Thus, in examples where the leaflets (e.g., 310 and 910) include one or more regions configured to support tissue ingrowth, such a configuration provides that tissue can grow across the interface between the leaflets and the supporting frame elements (e.g., the outer frame and the leaflet frame), thereby encouraging the tissue to grow onto and/or across the leaflet on either or both of the inflow and outflow sides of the leaflet. Finally, in such a configuration, the shoulder surface 1822 operates the support the leaflet 910 extending between the shoulder surface 1822 and the inflow edge 220 of the leaflet frame 200. In some examples, providing such support for the leaflet operates to minimize a potential for the leaflet 910 to decouple from the inflow edge 220 of the leaflet frame 200 when subjected to increased downstream fluid pressure, as those of skill should appreciate.

In some examples, in addition to or alternative to covering one or more of the outer frame (e.g., 800, 1800) and the leaflet frame (e.g., 200) with a material suitable for supporting tissue ingrowth, the outer frame and/or leaflet frame may include a surface modification to promote tissue ingrowth. In some examples, one or more of the leaflet frame and the outer frame could be formed of a porous PEEK material (injection moldable and/or machined) or a porous PEKK material (3D printable). Accordingly, one or more of the outer frame and the leaflet frame can be modified by choosing a favorable pore size and density to promote ingrowth where desired. In some examples, the leaflet frame and/or the outer frame any additionally include one or more non-growth regions. In certain instances, one or more portions of the material from which the outer frame and/or the leaflet frame are formed can be infused with a filler material to create such non-growth regions. The filler material may include any of the filler materials discussed herein.

In some examples, the leaflet frame 200 is supported on the shoulder surface 1822 of the second portion 1820 of the outer frame 1800. That is, in some examples, the second portion 1820 extends from the first portion 1818 and operates to support the leaflet frame 200.

Similar to the retention element 400 discussed above, the commissure post 1810 of the outer frame 1800 operates to secure the leaflet construct to the outer frame 1800 to form the prosthetic valve 100. In various examples, the leaflet construct is secured to the outer frame 1800 prior to the leaflet frame 200 being secured to the outer frame 1800, and/or prior to the leaflet construct (e.g., 900 or 300) being secured to the leaflet frame 200. In some such examples, the commissure posts 810 are disposed within the bridge loop (e.g., 938 or 338) of the leaflet construct (e.g., 900 or 300) prior to securing the leaflet construct to the outer frame 1800 and/or prior to securing the leaflet construct to the leaflet frame 200. Specifically, the commissure posts 1810 of the outer frame 1800 are operable to be disposed within the bridge loop (e.g., 938 or 338) formed by the bridge region 330 of the leaflet construct, thereby effectively preventing the bridge loop (e.g., 938 or 338) from passing through the post slot of 217 of the leaflet frame 200, as discussed above. In various examples, each commissure post 1810 has a width that is larger than a width of the post slot 217 of the leaflet frame 200. Moreover, as similarly discussed above, the size of the bridge loop (e.g., 938 or 338) should correspond to the size of the portion of the commissure post 1810 about which it is disposed to prevent excess material of the bridge region 330 from being pulled through the post slot 217, thereby changing a geometry of a corresponding leaflet.

The commissure post 1810 generally defines a relatively flat, rectangular cross section so as to have a low profile on the post outer side 212 of the commissure post 210 of the leaflet frame 200. In some example, the commissure post 1810 additionally includes a projection that is configured to extend between opposing coapting necks extending through a post slot 217 of the leaflet frame 200. For example, as shown in FIG. 11E, the commissure post 1810 of the outer frame 1800 includes a projection 1816 extending between leaflets 910 of the coaptation neck 940 passing through the post slot 217 of the leaflet frame 200. In some examples, the projection may extend entirely through the post slot 217. For example, the projection 1816 may be configured such that the projection 1816 extends away from the post inner side 1814 by an amount sufficient for the projection 1816 to extend radially inwardly of the leaflet frame inner side 202 (e.g., post inner side 214) when the leaflet frame 200 is coupled with the outer frame 1800. In some other examples, the projection may extend only partially into the post slot 217. For example, the projection 1816 may be configured such that the projection 1816 extends away from the post inner side 1814 by an amount sufficient for the projection 1816 to extend radially inwardly of the leaflet frame outer side 204 (post outer side 212) yet terminate radially outwardly of the leaflet frame inner side 202 (post inner side 214) when the leaflet frame 200 is coupled with the outer frame 1800. It will be appreciated that in some other examples, the projection 1816 may be configured to terminate at the leaflet frame inner side 204, or the leaflet frame outer side 202, or radially outwardly of the leaflet frame outer side 202.

In some examples, such a projection provides that a gap can be formed between adjacently situated leaflets at the commissure post 210. In some examples, the formation of such a gap can help minimize the potential for undesirable stasis at or proximate the commissure post 210. Accordingly, it will be appreciated that a width of the projection forming the gap can be increased or decreased to achieve a desired gap between coapting leaflets adjacent the commissure post 210. It will be appreciated that a width of the post slot 217 in the commissure post 210 of the leaflet frame 200 will generally correspond to the width of the projection 1816, such that the post slot 217 is configured to accommodate the projection 1816 and the plurality of leaflets (e.g., 910 or 310) extending therethrough. However, it will also be appreciated that, in some examples, it may undesirable to form a gap between coapting leaflets at the commissure post 210. In such instances, the commissure post 1810 of the outer frame 1800 may be configured without the incorporation of the projection 1816.

In accordance with embodiments, the commissure post 1810 can be flat, relatively flat, or concave on the inside (toward the center of the prosthetic valve 100) to correspond with the radially outer convexity of commissure post 210 that the commissure post 1810 will be adjacent to. In various example, similar to the retention elements 400, the commissure posts 1810 may include one or more apertures that align with commissure post apertures 209 wherein the commissure post 1810 is placed adjacent the post outer side 212 of the commissure post 210. Similarly, in some examples, a securement structure, such as, but not limited to suture 700, may be used to couple the commissure post 1810 to the commissure post 210. For example, as discussed above, stitching comprising suture 700 may be passed through aligned commissure post apertures 209 and apertures of the commissure post 1810, as well as through the bridge region of the leaflet construct to couple together each of the commissure post 1810, the leaflet construct, and the commissure post 210.

Each of the leaflet frame 200, the outer frame 1800, and the suture cuff 600 may be individually wrapped or covered with the fabric 1000 prior art being coupled one another. Alternatively, in some examples, the fabric 1000 may be coupled to or otherwise disposed about one or more of the leaflet frame 200, the outer frame 1800, and the suture cuff 600 after one or more of the leaflet frame 200, the outer frame 1800, and the suture cuff 600 have been coupled together. For example, the outer frame 1800 and the suture cuff 600 may be coupled together and then covered with the fabric 1000, after which the leaflet frame 200 is coupled with the outer frame 1800. Additionally, in various examples, the leaflet construct may be secured to the outer frame prior to (or alternatively after) the fabric is coupled to or otherwise disposed about the outer frame 1800.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed:

1. A prosthetic valve, comprising:
   a leaflet frame defining a cylinder and including a leaflet frame inner side, a leaflet frame outer side, a leaflet frame outflow edge, and a leaflet frame inflow edge, the leaflet frame further including a leaflet frame central axis and a plurality of leaflet frame commissure posts extending along the leaflet frame central axis, each leaflet frame commissure post defining a post slot therethrough such that the leaflet frame includes a plurality of post slots;
   a leaflet construct comprising a plurality of leaflets and a bridge region situated between adjacently situated leaflets, each bridge defining a bridge loop such that the leaflet construct defines a plurality of bridge loops, each bridge loop being situated adjacent to the leaflet frame outer side such that the leaflet construct extends through the plurality of post slots, each of the leaflets including a fold-over portion, the fold-over portion of each of the leaflets being folded around the inflow edge of the leaflet frame to the leaflet frame outer side; and
   an outer frame including a plurality of outer frame commissure posts, each outer frame commissure post being disposed within a first bridge loop of the plurality of bridge loops such that a portion of the first bridge loop is outside of the outer frame commissure post in a radial direction, the outer frame further including an outer frame inner side, an outer frame outer side, and an outer frame inflow edge, the leaflet frame being received with an interior region defined by the outer frame, wherein the leaflet frame outer side between the leaflet frame inflow edge and leaflet frame outflow edge of the leaflet frame is situated adjacent to and radially inwardly of the outer frame inner side, wherein the fold-over portion of the leaflet construct is positioned radially between the leaflet frame outer side and the outer frame inner side.

2. The prosthetic valve of claim 1, wherein the outer frame commissure posts include commissure post tips and wherein the leaflet frame is positioned between the outer frame commissure post tips and a shoulder surface of an annular shoulder of the outer frame.

3. The prosthetic valve of claim 1, wherein the outer frame comprises a plurality of keystones assembled to form the outer frame.

4. The prosthetic valve of claim 3, further comprising a ring element disposed about the outer frame.

5. The prosthetic valve of claim 1, wherein the outer frame includes a shoulder surface situated opposite the outer frame inflow edge and extending into the interior region defined by the outer frame transversely to the central axis, the shoulder surface operably supporting the leaflet frame inflow edge.

6. The prosthetic valve of claim 1, wherein the leaflet frame is coupled to the outer frame.

7. The prosthetic valve of claim 6, wherein the leaflet frame, the outer frame, and the leaflet construct each include a plurality of corresponding apertures, and wherein the leaflet frame and the outer frame are coupled together by a securement structure that passes through adjacent apertures of the leaflet frame, outer frame, and leaflet construct and is operable to couple the outer frame to the leaflet frame.

8. The prosthetic valve of claim 7, wherein the securement structure is a suture.

9. The prosthetic valve of claim 1, further comprising a sewing cuff coupled to the outer frame.

10. The prosthetic valve of claim 1, wherein the leaflet construct comprises an ePTFE composite.

11. The prosthetic valve of claim 10, wherein ePTFE composite comprises perfluorom ethyl vinyl ether and tetrafluoroethylene.

12. A prosthetic valve, comprising:
a leaflet frame including a leaflet frame inner side, a leaflet frame outer side, and a leaflet frame inflow edge, the leaflet frame further including a leaflet frame central axis and a plurality of leaflet frame commissure posts extending along the leaflet frame central axis, each leaflet frame commissure post defining a post slot therethrough such that the leaflet frame includes a plurality of post slots;
a leaflet construct comprising a plurality of leaflets and a bridge region situated between adjacently situated leaflets, each bridge defining a bridge loop such that the leaflet construct defines a plurality of bridge loops, each bridge loop being situated adjacent to the leaflet frame outer side such that the leaflet construct extends through the plurality of post slots,
an outer frame including an outer frame base and a plurality of outer frame commissure posts extending from the outer frame base, each outer frame commissure post being disposed within a first bridge loop of the plurality of bridge loops such that a portion of the first bridge loop is positioned outside of the outer frame commissure post in a radial direction, the outer frame commissure posts including a projection extending into the post slot of the leaflet frame and between two adjacent leaflets extending through the post slot of the leaflet frame.

13. The prosthetic valve of claim 12, wherein each of the leaflets including a fold-over portion, the fold-over portion of each of the leaflets being folded around the inflow edge of the leaflet frame to the leaflet frame outer side.

14. The prosthetic valve of claim 13, wherein the outer frame further includes an outer frame inner side, an outer frame outer side, an outer frame inflow edge, the leaflet frame being received with an interior region defined by the outer frame such that the fold-over portion of each of the leaflets is positioned between the outer frame inner side and the leaflet frame outer side, and such that the leaflet construct extends along the leaflet frame inflow edge.

15. The prosthetic valve of claim 14, wherein the projection is configured to extend away from an inner of the commissure post by an amount sufficient for the projection to extend radially inwardly of the leaflet frame inner side when the leaflet frame is coupled with the outer frame.

16. The prosthetic valve of claim 14, wherein projection extends only partially into the post slot of the leaflet frame such that an inner surface of the projection terminates radially outwardly of the leaflet frame inner side when the leaflet frame is coupled with the outer frame.

17. The prosthetic valve of claim 12, wherein each leaflet is secured to a first surface of the outer frame inner side.

* * * * *